US009173835B2

(12) United States Patent
Harel et al.

(10) Patent No.: US 9,173,835 B2
(45) Date of Patent: Nov. 3, 2015

(54) COMPOSITIONS AND METHODS FOR TREATING HYPERPROLIFERATIVE EPIDERMAL DISEASES

(75) Inventors: Avikam Harel, Tel Aviv (IL); Zeev Even-Chen, Rehovot (IL); Olga Bloch, Petach Tikva (IL)

(73) Assignee: Dermipsor Ltd., Katzrin (IL)

( * ) Notice: Subject to any disclaimer, the term of this patent is extended or adjusted under 35 U.S.C. 154(b) by 950 days.

(21) Appl. No.: 11/914,102

(22) PCT Filed: May 10, 2006

(86) PCT No.: PCT/IL2006/000553
§ 371 (c)(1),
(2), (4) Date: Jun. 10, 2008

(87) PCT Pub. No.: WO2006/120682
PCT Pub. Date: Nov. 16, 2006

(65) Prior Publication Data
US 2009/0131488 A1 May 21, 2009

Related U.S. Application Data

(60) Provisional application No. 60/679,556, filed on May 10, 2005.

(51) Int. Cl.
| *A61K 31/593* | (2006.01) |
| *A61K 9/00* | (2006.01) |
| *A61K 31/455* | (2006.01) |
| *A61K 31/59* | (2006.01) |
| *A61K 45/06* | (2006.01) |
| *A61K 47/10* | (2006.01) |

(52) U.S. Cl.
CPC ............. *A61K 9/0014* (2013.01); *A61K 31/455* (2013.01); *A61K 31/59* (2013.01); *A61K 31/593* (2013.01); *A61K 45/06* (2013.01); *A61K 47/10* (2013.01)

(58) Field of Classification Search
USPC ........................... 514/167, 356, 729; 552/653
See application file for complete search history.

(56) References Cited

U.S. PATENT DOCUMENTS

| 4,067,975 | A | | 1/1978 | Yu et al. .......................... 424/240 |
| 4,424,075 | A | * | 1/1984 | Schmidt ................... 106/287.12 |
| 4,434,183 | A | | 2/1984 | McGraw et al. ............... 424/340 |
| 4,594,432 | A | * | 6/1986 | Baggiolini et al. ............ 549/214 |
| 4,719,205 | A | * | 1/1988 | DeLuca et al. ................. 514/167 |
| 4,804,502 | A | | 2/1989 | Baggiolini et al. ......... 260/397.2 |
| 4,851,401 | A | | 7/1989 | DeLuca et al. ................. 514/167 |
| 4,855,142 | A | * | 8/1989 | Fankhauser et al. ........... 424/434 |
| 4,857,518 | A | | 8/1989 | DeLuca et al. ................. 514/167 |
| 4,866,048 | A | | 9/1989 | Calverley et al. .............. 514/167 |
| RE33,107 | E | * | 11/1989 | Dikstein et al. .................. 514/46 |
| 5,037,816 | A | | 8/1991 | Holick et al. .................. 514/167 |
| 5,120,722 | A | | 6/1992 | Baggiolini et al. ............ 514/167 |
| 5,145,846 | A | | 9/1992 | Baggiolini et al. ............ 514/167 |
| 5,194,248 | A | | 3/1993 | Holick |
| 5,237,110 | A | | 8/1993 | DeLuca et al. ................. 568/665 |
| 5,254,331 | A | * | 10/1993 | Mausner .......................... 424/59 |
| 5,374,629 | A | | 12/1994 | Calverley et al. .............. 514/167 |
| 5,403,940 | A | | 4/1995 | Vallés et al. .................... 549/300 |
| 5,411,949 | A | | 5/1995 | Neef et al. ...................... 514/167 |
| 5,430,049 | A | | 7/1995 | Gaut ............................... 514/410 |
| 5,431,925 | A | | 7/1995 | Ohmori et al. ................. 424/646 |
| 5,446,034 | A | | 8/1995 | Bretting et al. ................ 514/167 |
| 5,446,035 | A | | 8/1995 | Neef et al. ...................... 514/167 |
| 5,447,924 | A | | 9/1995 | Bretting ......................... 514/167 |
| 5,519,059 | A | * | 5/1996 | Sawaya .......................... 514/599 |
| 5,747,479 | A | | 5/1998 | Bryce et al. .................... 514/167 |
| 5,789,399 | A | | 8/1998 | Strube |
| 5,804,574 | A | | 9/1998 | Bryce et al. .................... 514/167 |
| 5,811,414 | A | | 9/1998 | Bryce et al. .................... 514/167 |
| 5,831,074 | A | | 11/1998 | Strumwasser et al. ..... 536/26.23 |
| 5,834,016 | A | | 11/1998 | Naeff et al. |
| 5,914,334 | A | | 6/1999 | Charu |
| 6,107,349 | A | | 8/2000 | Mantynen ...................... 514/863 |
| 6,231,875 | B1 | | 5/2001 | Sun et al. |
| 6,242,435 | B1 | | 6/2001 | Achkar |
| 6,248,763 | B1 | | 6/2001 | Scivoletto ...................... 514/356 |
| 6,262,041 | B1 | | 7/2001 | Serbinova ...................... 514/167 |
| 6,284,234 | B1 | | 9/2001 | Niemiec et al. ............. 424/78.07 |
| 6,288,249 | B1 | | 9/2001 | Halkes et al. .................. 552/653 |
| 6,429,218 | B1 | | 8/2002 | Scivoletto et al. ............. 514/356 |
| 6,552,009 | B2 | | 4/2003 | Achkar .......................... 514/168 |
| 6,730,288 | B1 | | 5/2004 | Abram ............................. 424/45 |
| 6,753,013 | B1 | | 6/2004 | Didriksen et al. ............. 424/484 |
| 6,787,529 | B2 | | 9/2004 | Hoy et al. |
| 6,831,106 | B1 | | 12/2004 | Bernardon et al. ............ 514/730 |
| 6,890,904 | B1 | * | 5/2005 | Wallner et al. ................... 514/14 |
| 7,259,138 | B2 | * | 8/2007 | Wallner et al. .................... 514/2 |
| 2003/0032617 | A1 | * | 2/2003 | Harel et al. ....................... 514/46 |
| 2004/0092583 | A1 | * | 5/2004 | Shanahan-Prendergast . 514/469 |
| 2004/0138184 | A1 | | 7/2004 | Schwartz et al. .............. 514/167 |
| 2006/0275218 | A1 | | 12/2006 | Tamarkin et al. |
| 2007/0003614 | A1 | * | 1/2007 | Chen et al. ..................... 424/456 |
| 2008/0069779 | A1 | | 3/2008 | Tamarkin et al. |
| 2008/0312181 | A1 | | 12/2008 | Harel et al. ....................... 514/47 |
| 2009/0098065 | A1 | | 4/2009 | Harel et al. ....................... 514/47 |

FOREIGN PATENT DOCUMENTS

| DE | 4335454 A1 | 4/1995 | ............. A61K 35/78 |
| DE | 29916231 | 2/2000 | ............. A61K 33/00 |

(Continued)

OTHER PUBLICATIONS

Norio, Takasugi et al. (JP 05-271080, English translation).*

(Continued)

*Primary Examiner* — Sabiha N Qazi
(74) *Attorney, Agent, or Firm* — Winston & Strawn LLP

(57) ABSTRACT

The present invention provides compositions and methods for use in the treatment of hyperproliferative dermal diseases. Specifically, the present invention teaches pharmaceutical compositions for topical administration where the compositions contain nicotinamide and a vitamin D metabolite, calcipotriol, which are particularly effective in treating and in the maintenance treatment of psoriasis and other related dermal disorders and diseases.

9 Claims, 3 Drawing Sheets

(56) References Cited

FOREIGN PATENT DOCUMENTS

| | | | |
|---|---|---|---|
| EP | 052705 | 6/1982 | ........... A61K 31/455 |
| EP | 177920 | 4/1986 | ............ A61K 31/59 |
| HU | 209067 | 3/1994 | |
| JP | 08-073338 A | 3/1996 | |
| JP | 10139669 | 3/1998 | ............... A61K 9/08 |
| JP | 2002-527356 | 8/2002 | |
| WO | WO87/00834 A1 | 2/1987 | |
| WO | WO 96/00074 | 1/1996 | ............. A61K 31/59 |
| WO | WO 98/52529 | 11/1998 | ............... A61K 7/48 |
| WO | WO 00/03700 | 1/2000 | ............. A61K 31/07 |
| WO | WO 00/64450 | 11/2000 | ............. A61K 31/59 |
| WO | WO 01/00164 | 1/2001 | ............... A61K 7/50 |
| WO | WO 01/51051 | 7/2001 | |
| WO | WO 2004/006887 A2 | 1/2004 | |
| WO | WO 2004/037225 | 5/2004 | ............... A61K 9/00 |
| WO | WO2008/031734 A1 | 3/2008 | |

OTHER PUBLICATIONS

Christina Mark Hansen et al. (Frontiers of Bioscience 6, d820-848, Jult 1, 2001).*
K. W. Colston and Mark Hansen (Endocrine-Related Cancer (2001) 9, 45-59).*
Stuttgen (Stuttgen Clinics in Dermatology (1997), vol. 15, pp. 693-703).*
Takasugi Norio et al.—JP-05-271080A (English translation).*
Yoshihiko, M et al. (abstract JP 10139669 (A)).*
Working et al. (Book, Publication date Aug. 5, 1997. In Poly(ethylene glycol); Harris, J. et al. ACS Symposium Series; American Chemical Society SYmposium, DC 1997—p. 45-57).*
Bosman, Brigitte et al., (1992) A quantitative method for measuring antipsoriatric activity of drugs by the mouse-tail model. Skin Pharmacology and Physiology 5:41-48.
Dick, Ian P. and Scott, Robert C. (1992) Pig ear skin as an in-vitro model for human skin permeability. *J Pharm Pharmacol* 44(8):640-645.
Feldman, S. R. and Krueger, G. G. (2005) Psoriasis assessment tools in clinical trials. *Ann Rheum Dis* 64(Suppl 2):ii65-ii68.
Gottlieb, Alice B. et al., (2003) The National Psoriasis Foundation Psoriasis Score (NPF-PS) system versus the Psoriasis Area Severity Index (PASI) and Physician's Global Assessment (PGA): a comparison. *J Drugs Dermatol.* 2(3):260-266.
Harel, Avikam et al., (2002) Sensitivity of HaCat keratinocytes to diabetogenic toxins. Biochem Pharmacol. 63(2):171-178.
Holick, Michael F. Vitamin D: Cutaneous production and therapeutic efficacy in psoriasis. Proceedings of the workshop on vitamin D 1991 8$^{th}$ (vitamin D), 940-948.
Kragballe, K. et al., (2006) A 52-week randomized safety study of a calcipotriol/betamethasone dipropionate two-compound product (Dovobet®/Daivobet®/Taclonex®) in the treatment of psoriasis vulgaris. *Br J Dermatol* 154(6):1155-1160.
Morimoto, S. et al., (1986) An open study of vitamin $D_3$ treatment in psoriasis vulgaris. *Br. J. Dermatol* 115(4):421-429.
Murdoch, David and Clissold, Stephen P. (Mar. 1992) Calcipotriol: A Review of its Pharmacological Properties and Therapeutic Use in Psoriasis Vulgaris. *Drugs* 43(3):415-429.
Otonkoski, Timo et al., (1993) Nicotinamide is a potent inducer of endocrine differentiation in cultured human fetal pancreatic cells. *J Clin Invest.* 92(3):1459-1466.
Shalita, A. R. et al., (1995) Topical nicotinamide compared with clindamycin gel in the treatment of inflammatory acne vulgaris. *Int J Dermatol.* 34(6):434-437.
Simon, Gad A. and Maibach, Howard I. (2000) The pig as an experimental animal model of percutaneous permeation in man: qualitative and quantitative observations—an overview. *Skin Pharmacol Appl Skin Physiol.* 13(5):229-234.
Stuttgen, Gunter, History of Treatments, Clinics in Dermatology, vol. 15, pp. 693-703 (1997).
Michel, G. et al.,1,25-(OH)2-tain 3and cicipotrol induc IL-10 receptor geneexpression in human epidermal cells, Inflamm. Res., vol. 46, pp. 32-34 (1997).
Non-Final Office Action, U.S. Appl. No. 11/914,093, dated Jun. 29, 2010.
Non-Final Office Action, U.S. Appl. No. 11/914,093, dated Dec. 10, 2010.
Non-Final Office Action, U.S. Appl. No. 12/242,243 dated Jan. 20, 2011.
Ben-Shabat et al., (2005) Vitamin D3—Based Conjugates for Topical Treatment of Psoriasis: Synthesis, Antiproliferative Activity, and Cutaneous Penetration Studies. Pharmaceutical Research 22(1): 50-57.
DeLuca (1988) The vitamin D story: a collaborative effort of basic science and clinical medicine. FASEB J 2(3): 224-236.
Fitzpatrick et al., Dermatology in General Medicine, vol. 1, 4th edition, 1993, McGraw-Hill Inc.. 504-5, 531-2,709,1821-1882.
Lehmann et al., (2004) Vitamin D and skin: new aspects for dermatology. Exp Dermatol; 13 Suppl 4: 11-15.
Levine (2010) Pilot, multicenter, double-blind, randomized placebo-controlled bilateral comparative study of a combination of calcipotriene and nicotinamide for the treatment of psoriasis. J Am Acad Dermatol 63(5): 775-781.
Glenville Jones,"Metabolism and Catabolism of Vitamin D, its Metabolites, and Clinically Relevant Analogs", in Vitamin D: Physiology, Molecular Biology and Clinical Applications, edited by M.F. Holick, Humana Press,1999.
Masami Okabe, "Chemistry of Vitamin D: A Challenging Field for Process Research", in Process Chemistry in the Pharmaceutical Industry, edited by Kumar G. Gadamasetti, Marcel Dekker, Inc., 1999.
Nomenclature of Vitamin D, Recommendations 1981. Issued by the International Union of Pure and Applied Chemistry and International Union of Biochemistry and Molecular Biology, IUPAC-IUB Joint Commission on Biochemical Nomenclature (JCBN).
Abstract- XP002041731: Dermtaological prepn. contg. water soluble deriv. Of retinol—useful for treating hyper-keratosis and preventing wrinkles is safe and stable, WPI World Patent Information Derwent, GB, vol. 21, No. 96 PA—Noevir PN—JP8073338 A, Mar. 19, 1996.

\* cited by examiner

COMPOSITIONS AND METHODS FOR TREATING HYPERPROLIFERATIVE EPIDERMAL DISEASES

This application is a 371 of International application no. PCT/IL2006/000553 filed May 10, 2006, which claims the benefit of U.S. provisional application no. 60/679,556 filed May 10, 2005.

FIELD OF THE INVENTION

The present invention relates to compositions useful for the treatment of hyperproliferative dermal diseases. Specifically, the present invention provides a topical composition consisting essentially of vitamin D metabolite, calcipotriol, and nicotinamide, which is particularly effective in treating psoriasis and other related dermal disorders and diseases.

BACKGROUND OF THE INVENTION

Hyperproliferative Skin Disorders and Diseases

Hyperproliferative skin disorders refers to a set of diseases and disorders, which are characterized by a higher than normal level of proliferation of epidermal cells known as keratinocytes, and, as a rule, also by abnormal differentiation.

The hyperproliferative epidermal pathology may be malignant or benign. Malignant hyperproliferative epidermal pathologies include: squamous-cell carcinoma (SCC), basal-cell carcinoma (BCC) and other non-melanoma skin cancers (NMSCs). Representative examples of benign hyperproliferative epidermal pathologies include psoriasis, common warts, keratoacanthoma, seborrhoeic keratosis, seborrhea and ichthyosis.

Psoriasis is a non-contagious skin disorder affecting up to 2% of the world's population. It is estimated that ten million in the U.S. and Europe suffer from psoriasis and up to 260,000 new cases are diagnosed each year. In the U.S. alone there are over 1,500,000 clinic visits per year for psoriasis and the annual outpatient costs are currently estimated to be about US $2 billion.

Psoriasis is caused by unknown factors that stimulate T-lymphocyte activation, proliferation, and cytokine release that leads to hyperproliferation of keratinocytes. Although the etiology of psoriasis is unknown, the affected keratinocytes are responsible for the typical clinical features of the disease: well-demarcated inflamed skin lesions covered with a silvery white scale, covering about 10%-15% of the body surface. Psoriasis primarily affects adults and may manifest itself in different variations and degrees of severity.

The main strategy for the treatment of hyperproliferative skin diseases, including psoriasis, is to prevent excessive keratinocyte division and to stimulate cell differentiation.

At present there are three modalities of treatment for psoriasis:

1) Topical administration of therapeutic cream or ointment, for treating mild and moderate cases;

2) Phototherapy (UVA or UVB) used alone or in combination with medication or topical treatment, requires repeated visits to the clinic and exposes the patient to the concomitant dangers of radiation;

3) Systemic treatment, relying on immunosuppressive therapy, is limited to severe cases due to the serious side effects.

Vitamin D and Hyperproliferative Skin Disease

Vitamin D is a prohormone with several active metabolites that act as hormones. In the skin, previtamin $D_3$ is synthesized photochemically from 7-dehydrocholesterol and is slowly isomerized to vitamin $D_3$, which is removed by vitamin D-binding protein. In the liver, vitamin $D_3$ is converted to $25(OH)D_3$, the major circulating form, which passes through the enterohepatic circulation and is reabsorbed from the gut. In the kidneys, it is further hydroxylated to the more metabolically active form, $1\alpha,25(OH)_2D_3$ ($1\alpha,25$-dihydroxycholecalciferol, calcitriol, vitamin D hormone).

Experimental evidence has shown that vitamin D functions as an anti-proliferative agent and stimulates the terminal differentiation of keratinocytes. In psoriatic lesions, epidermal keratinocytes exhibit hyperproliferation and impaired differentiation triggered by inflammation. Therefore, vitamin D and certain analogs are effective in treating psoriasis vulgaris (reviewed in DeLuca 1988; Lehmann et al., 2004). The systemic administration of these compounds is limited by their toxicity and adverse effect on calcium metabolism, therefore topical preparations are preferred.

Calcipotriol (calcipotriene), a vitamin $D_3$ derivative is marketed in the United States as a topical antipsoriatic under the trade name Dovonex® (USA) or Daivonex® (Europe). Calcipotriol is as potent as the naturally occurring calcitriol in regulating cell proliferation, but has the benefit of being much less active in its effect on calcium metabolism. Despite this, calcipotriol is only partially effective in treating psoriatic lesions.

The art provides some examples of vitamin D analogs and derivatives and compositions comprising the same.

Vitamin D analogs are described in U.S. Pat. No. 4,851,401 (cyclopentano-vitamin D analogs), U.S. Pat. No. 5,120,722 (trihydroxycalciferol derivatives), U.S. Pat. No. 5,446,035 (20-methyl substituted vitamin D), U.S. Pat. No. 5,411,949 (23-oxa-derivatives), U.S. Pat. No. 5,237,110 (19-nor-vitamin D compounds), U.S. Pat. No. 4,857,518 (hydroxylated 24-homo-vitamin D derivatives). Additional Vitamin D analogs are taught in U.S. Pat. Nos. 4,804,502; 4,866,048; 5,145,846 5,374,629; 5,403,940; 5,446,034; and 5,447,924.

U.S. Pat. No. 5,037,816 is directed to a method of treating psoriasis which comprises topically administering an effective amount of a vitamin D compound which is capable of stimulating the differentiation of cultured tumor cells or normal rodent or human fibroblasts or keratinocytes in vitro.

U.S. Pat. No. 6,552,009 discloses a composition comprising a vitamin D analog and a derivative of retinoid useful in treating disorders characterized by abnormal cell-proliferation and/or cell-differentiation. In certain preferred embodiments the vitamin D analog is selected from calcitriol and calcipotriol.

U.S. Pat. No. 6,753,013 describes a pharmaceutical composition for dermal use comprising a combination of a vitamin D analog and a corticosteroid, the composition alleviating the inconvenience of a two-component regimen for the treatment of psoriasis and other inflammatory skin diseases.

Nicotinamide

Nicotinamide (NA, niacinamide), a derivative of vitamin $B_3$ and a precursor of the coenzyme nicotinamide adenine dinucleotide (NAD), displays multiple functions in cell metabolism. NA has been shown to induce the differentiation of insulin-producing cells (Otonkoski et al, 1993) and the protection of the pancreatic beta-cells from genotoxic agents (Pipeleers and Van de Winkel, 1986). U.S. Pat. No. 6,248,763 relates to specific topical compositions for treating skin conditions for example acne and psoriasis, which comprise 0.01%-1% methyl nicotinate, as the active ingredient.

The synergistic effects of NA and vitamin D metabolites on differentiation and proliferation of human epidermal cells have recently been reported by some of the present inventors.

International Patent Application Publications WO 01/51051 and WO 2004/006887 of some of the present inventors are directed to compositions and methods of treating a benign or malignant hyperproliferative epidermal pathology comprising administering to the subject a therapeutically effective amount of an agent selected from the group consisting of nicotinamide and/or cyclic adenosine diphosphate-ribose (cADPR), and analogs thereof. The applications also disclose the combination of vitamin $D_3$ metabolite (1α 25($OH_2$) $D_3$) and NA and its synergistic effect on the differentiation and proliferation of human epidermal cells.

Vitamin $D_3$ and vitamin $D_3$ analogs are known to possess anti-proliferative and prodifferentiating properties and are therefore effective in the treatment of hyperproliferative skin disorders, for example psoriasis vulgaris. The synergistic effect of vitamin $D_3$ with nicotinamide to further inhibit proliferation of keratinocytes has been demonstrated by some of the inventors of the present invention. Although a synergistic inhibitory effect of vitamin $D_3$ and nicotinamide has been shown in keratinocytes in vitro, optimization of the two components in a pharmaceutical composition has never been shown.

The art has neither taught nor suggested specific formulations consisting essentially of a vitamin $D_3$ analog and a nicotinamide analog for the prevention, treatment or attenuation of disorders associated with hyperproliferative skin diseases.

There remains a yet unmet medical need for compositions and methods useful in preventing and treating the symptoms associated with hyperproliferative disease, and in particular, psoriasis.

SUMMARY OF THE INVENTION

The present invention provides compositions consisting essentially of a vitamin $D_3$ analog and nicotinamide, and methods of use thereof for the treatment of hyperproliferative disease. In particular, the inventors of the present invention have unexpectedly found that vitamin D metabolite, calcipotriol, when provided in combination with nicotinamide, produces a synergistic effect in reducing the symptoms of hyperproliferative disease in a specific concentration range. Accordingly, the present invention provides highly efficacious therapeutic compositions consisting essentially of calcipotriol and nicotinamide, at defined concentration ranges.

Additionally, the invention discloses that, in contradistinction to known formulations comprising calcipotriol, the calcipotriol in the present composition does not significantly penetrate the skin, thereby precluding systemic exposure to the drug and concomitant side effects. The composition of the present invention is therefore unexpectedly useful in the immediate treatment of hyperproliferative disease as well as for long-term maintenance therapy.

The compositions of the present invention have been formulated to be highly efficacious and safe in the inhibition of cell proliferation, in particular of skin cells, and more particularly of keratinocytes and are thus useful in the treatment of psoriasis and other hyperproliferative skin diseases.

In one aspect the present invention provides a pharmaceutical composition for topical administration useful in treating hyperproliferative skin diseases and disorders consisting essentially of:
- calcipotriol at a concentration of about 10 µg/g (micrograms per gram) to about 100 µg/g;
- nicotinamide at a concentration of about 0.1 mg/g to about 50 mg/g; and
- a dermatologically acceptable excipient or carrier.

In some embodiments the composition is provided in a form selected from the group consisting of an aqueous solution, a non-aqueous solution, a lotion, a cream, a gel, an ointment, foam, mousse, a spray, an emulsion and a microemulsion.

In certain embodiments the composition is provided in the form of a dermal ointment, cream, lotion or gel.

In some embodiments the dermatological excipient comprises polyethylene glycol (PEG). In some embodiments PEG is selected from PEG-400, PEG-4000 and a mixture of the two. Preferably the composition comprises a mixture of PEG-400 and PEG-4000.

In some embodiments the carrier further comprises a surfactant. One non-limiting example of a suitable surfactant is polyoxyethylated stearyl alcohol (steareth). In preferred embodiments the dermatological carrier comprises PEG-400, PEG-4000 and Steareth 20. In some embodiments the composition of the present invention consists essentially of calcipotriol, nicotinamide, PEG and Steareth-20.

In specific embodiments the dermal composition has the following formulation:
- about 10 µg/g to about 100 µg/g calcipotriol;
- about 0.5 to about 25 mg/g nicotinamide;
- about 70% to about 80% (w/w) PEG-400;
- about 15% to about 25% (w/w) PEG-4000;
- about 1% to about 5% (w/w) Steareth-20;
- about 0.1 to about 1% (w/w) vitamin E.

In some embodiments calcipotriol is provided at a concentration of about 20 µg/g to about 70 µg/g. In specific embodiments calcipotriol is provided at a concentration of about 50 µg/g.

In other embodiments calcipotriol is provided at a concentration of about 10 µg/g to about 50 µg/g, preferably at a concentration of about 15 µg/g to about 35 µg/g. In some embodiments calcipotriol is provided at a concentration of about to about 30 µg/g.

In some embodiments nicotinamide is provided at a concentration of about 0.5 mg/g to about 25 mg/g. In certain embodiments the nicotinamide is provided at a concentration of about 1 mg/g to about 20 mg/g. In other embodiments the nicotinamide is provided at a concentration of about 2 mg/g to about 10 mg/g. In specific embodiments nicotinamide is provided at a final concentration of about 2.1 mg/g.

Accordingly, the present invention provides a PEG-based ointment for topical administration useful in treating hyperproliferative skin diseases and disorders consisting essentially of:
- calcipotriol at a concentration of about 50 µg/g;
- nicotinamide at a concentration of about 2.1 mg/g; and
- a dermatologically acceptable PEG-based excipient or carrier.

In some embodiments the hyperproliferative skin disease is a benign hyperproliferative disease selected from psoriasis, solar (actinic) keratosis, ichthyosis, Grover's disease (transient acantholytic dermatosis), common warts, keratoacanthoma, seborrhoeic keratosis, scleroderma, and seborrhea.

In other embodiments the hyperproliferative skin disease is a malignant hyperproliferative skin disease. Representative examples of malignant hyperproliferative epidermal pathologies include, without limitation, squamous-cell carcinoma (SCC), basal-cell carcinoma (BCC) and other non-melanoma skin cancers (NMSCs).

In specific embodiments the hyperproliferative disease is psoriasis.

In another aspect the present invention provides a method of preventing or treating a hyperproliferative skin disease or disorder comprising the step of:

topically administering to a subject in need thereof a therapeutically effective amount of a composition consisting essentially of calcipotriol at a concentration of about 10 µg/g to about 100 µg/g; nicotinamide at a concentration of about 0.1 mg/g to about 50 mg/g; and a dermatologically acceptable excipient or carrier.

The method preferably comprises topical administration up to about four times daily of a therapeutically sufficient dosage of said composition. In specific embodiments the composition is administered once or twice daily. In some embodiments the composition is applied twice daily at intervals of about 12 hours. In other embodiments the composition is administered once daily.

In some embodiments the method of treatment includes two treatment periods: an initial treatment, and a maintenance treatment. First, in the initial treatment a patient administers an initial dosage of the composition consisting essentially of calcipotriol at a concentration of about 10 µg/g to about 100 µg/g; nicotinamide at a concentration of about 0.1 mg/g to about 50 mg/g; and a dermatologically acceptable excipient or carrier for an initial period and thereafter, the patient administers a lower maintenance dosage of a composition consisting essentially of calcipotriol at a concentration of about 10 µg/g to about 50 µg/g; nicotinamide at a concentration of about 0.1 mg/g to about 50 mg/g; and a dermatologically acceptable excipient or carrier.

For the maintenance dosage, the calcipotriol is provided at a concentration of about 10 µg/g to about 50 µg/g. In yet other embodiments calcipotriol is provided at a concentration of about 15 µg/g to about 35 µg/g. In specific embodiments calcipotriol is provided at a concentration of about 30 µg/g.

In some embodiments nicotinamide is provided at a concentration of about 0.5 mg/g to about 25 mg/g. In certain embodiments nicotinamide is provided at a concentration of about 1 mg/g to about 20 mg/g. In other embodiments nicotinamide is provided at a concentration of about 2 mg/g to about 10 mg/gm, preferably at a concentration of about 2.1 mg/g.

According to certain preferred embodiments the present invention provides a method of preventing or treating a hyperproliferative skin disease or disorder comprising the steps of:

topically administering to a subject in need thereof a therapeutically effective amount of a composition consisting essentially of calcipotriol at a concentration of about 10 µg/g to about 100 µg/g; nicotinamide at a concentration of about 0.5 mg/g to about 25 mg/g; and a dermatologically acceptable excipient or carrier for an initial period of time to reduce the symptoms of the hyperproliferative disease; and topically administering to a subject in need thereof a therapeutically effective amount of a composition consisting essentially of calcipotriol at a concentration of about 10 µg/g to about 50 µg/g; nicotinamide at a concentration of about 0.5 mg/g to about 25 mg/g; and a dermatologically acceptable excipient or carrier for a second period of time.

In one embodiment the initial period of time is about 4 weeks to about 24 weeks, preferably from about 4 weeks to about 16 weeks. In certain preferred embodiments the initial treatment period is from about 6 weeks to about 12 weeks, preferably about 8 weeks. The second period of time is about 8 weeks to about 52 weeks, preferably from about 12 weeks to about 26 weeks.

In certain embodiments the subject is a mammal. In specific embodiments the subject is a human subject.

In yet another aspect the present invention provides a composition comprising calcipotriol, wherein the calcipotriol does not significantly penetrate the skin. In certain embodiments less than 10% of the calcipotriol penetrates the skin, preferably less than 5%. In some embodiments less than 3% and preferably less than 1% of the calcipotriol penetrates the skin.

In some embodiments the composition consists essentially of calcipotriol, at least one PEG and a surfactant. In specific embodiments the composition consists essentially of calcipotriol, PEG-400, PEG-4000 and Steareth-20.

The present invention further provides the use of a composition consisting essentially of calcipotriol at a concentration of about 10 µg/g (micrograms per gram) to about 100 µg/g; and nicotinamide at a concentration of about 0.1 mg/g to about 50 mg/g; to prepare a therapeutical composition for the topical treatment of hyperproliferative disease.

The present invention further provides a composition of the present invention packaged in a container suitable for dispensing of said composition; and written instructions for use.

Hence, according to further aspects of the present invention there are provided pharmaceutical kits, which comprise a composition consisting essentially of calcipotriol at a concentration of about 10 µg/g to about 100 µg/g;

nicotinamide at a concentration of about 0.1 mg/g to about 50 mg/g;

a dermatologically acceptable excipient or carrier;

and instructions for use.

According to certain preferred embodiments the present invention provides a kit comprising a topical composition consisting essentially of calcipotriol at a concentration of about 50 µg/g; nicotinamide at a concentration of about 2.1 mg/g; a dermatologically acceptable excipient or carrier; and instructions for use.

According to other preferred embodiments the kit further comprises a topical composition consisting essentially of calcipotriol at a concentration of about 10 µg/g to about 50 µg/g; nicotinamide at a concentration of about 2.1 mg/g; and a dermatologically acceptable excipient or carrier; and instructions for use. Preferred concentrations of calcipotriol are about 15 µg/g to about 35 µg/g, preferably about 30 µg/g.

These and other embodiments of the present invention will become apparent in conjunction with the figures, description and claims that follow.

BRIEF DESCRIPTION OF THE FIGURES

FIG. 1A is a graph that shows the level of orthokeratosis induced by the different stable ointment formulations. FIG. 1B is a graph that shows the drug activity of the stable ointment formulations. The formulations comprise 50 µg/g calcipotriol and 0.61 mg/g of NA.

FIG. 2A is a graph showing the optimization of the NA concentration in the ointment formulation, as determined by an increase in orthokeratosis.

FIG. 2B is a graph showing the drug activity of the formulations with 50 µg/g calcipotriol and different concentrations of NA, derived from FIG. 2A.

DETAILED DESCRIPTION OF THE INVENTION

Figure 1A:
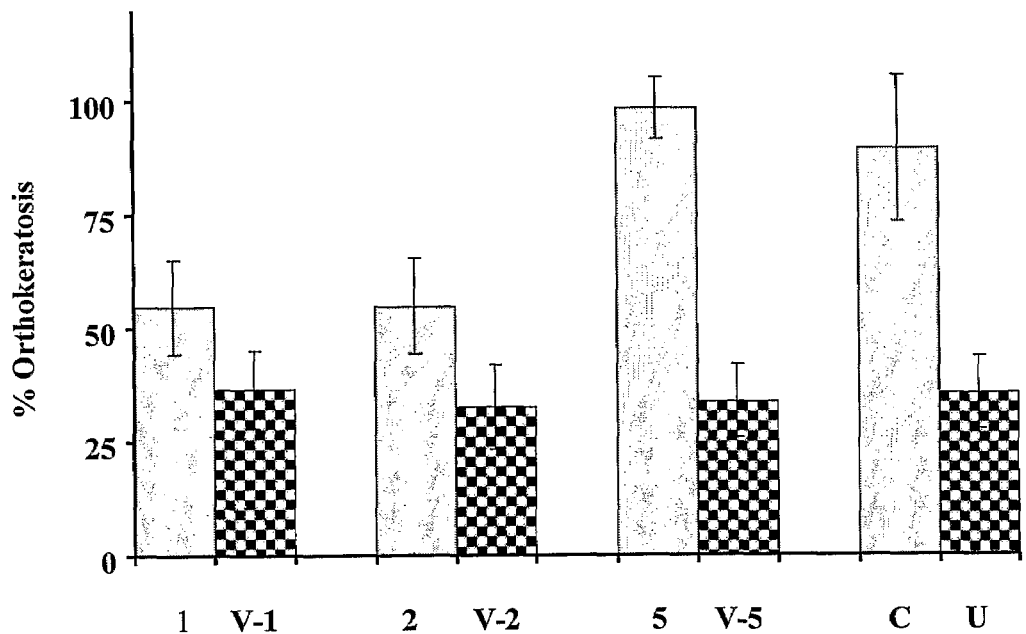
FIGS. 1A-1B.

The present invention is directed to pharmaceutical compositions, kits and methods, which can be used in the treatment skin disorders related to hyperproliferation of epidermal cells.

As is described hereinabove, vitamin $D_3$ and its analogs are known as useful agents in the treatment of psoriasis and other inflammatory skin diseases (Morimoto et al., 1986). Nicotinamide and its analogs have been shown to be effective in inhibiting hyperproliferation of keratinocytes and in the induction of cell differentiation. The present invention provides dermal compositions consisting essentially of a vitamin D derivative, calcipotriol, and nicotinamide, which is highly efficacious in the treatment of hyperproliferative skin diseases and disorders.

A composition combining calcipotriol and NA provides synergy in the form of additional benefit to the patient apart from the direct therapeutic value of the individual active substances.

Satisfactory medical treatment of skin disorders, such as psoriasis, can be attained in a shorter period of time using the composition according to the invention. Furthermore the composition of the present invention does not contain steroids, thus obviating the side effects associated with that class of drugs.

The composition of the present invention provides a safe, effective topical formulation for the treatment of hyperproliferative diseases and offers the following advantages over the commercially available calcipotriol compositions:

a) Dual anti-proliferative and differentiation-promoting effect on epidermal cells;

b) Synergetic therapeutic effect of the calcipotriol and nicotinamide, which intensifies the potential therapeutic effect of the composition for benign and malignant hyperproliferative disorders;

c) Anti-oxidative effect;

d) Non-toxic formulation approved for topical indications;

e) Calcipotriol in the present formulation does not penetrate the skin, thereby precluding systemic exposure to the drug and concomitant side effects;

f) The calcipotriol-nicotinic acid formulation of the invention was classified as a negligible irritant, whereas the commercially available products are labeled as irritants;

g) Avoidance of steroid and corticosteroid compounds and concomitant side effects.

Definitions

For convenience and clarity certain terms employed in the specification, examples and claims are described herein.

As used herein, the phrase "effective amount" and "therapeutically effective amount" describes an amount of the agent that is sufficient to substantially abrogate, alleviate, inhibit, reduce or prevent the symptoms of hyperproliferative disease. Symptoms of psoriasis include one or more of dermatological inflammation; red, flaky skin; rash; itching; plaques; blisters.

According to the present invention, final concentrations of the calcipotriol typically range between 10 µg/g and 100 µg/g composition, preferably between about 20 µg/g and 70 µg/g. In specific compositions, calcipotriol is provided at a concentration of about 50 µg/g.

In some embodiments a composition comprising a final concentration of about 10 µg/g to about 50 µg/g. calcipotriol is suitable for maintenance therapy of dermal hyperproliferative disease. In some embodiments a final concentration of about 15 µg/g to about 35 µg/g calcipotriol, preferably about 30 µg/g calcipotriol, is provided.

The term "does not significantly penetrate the skin" refers to a composition comprising calcipotriol, wherein less than about 10% of the calcipotriol in the composition penetrates the skin cells, as determined for example, in a porcine ear skin cell assay. In some embodiments less than 5%, preferably less than 3% and more preferably less than 1% of the calcipotriol penetrates the skin. The adverse systemic affects of vitamin $D_3$ are well known in the art and a composition, which precludes the penetration of calcipotriol into the skin cells, is highly desired.

"Maintenance therapy" refers to treatment to either prevent the recurrence or relapse or to prevent the progression of symptoms associated with hyperproliferative disease. Nicotinamide (niacinamide) is one of the two principal forms of the B-complex vitamin $B_3$ niacin. Some of the inventors of the present invention have identified NA as a inhibitor of cell proliferation, in particular of keratinocytes. According to the present invention, final concentrations of NA typically range between 0.1 mg/g and 25 mg/g composition, preferably between about 1 mg/g and 20 mg/g. In specific compositions NA is provided at a concentration of about 2 mg/g to about 10 mg/g and more preferably at a concentration of 2 mg/g to about 6.5 mg/g. A preferable concentration is 2.1 mg/g.

Herein, the term "treating" includes abrogating, substantially inhibiting, slowing or reversing the progression, substantially ameliorating clinical symptoms, or substantially preventing the appearance of symptoms associated with hyperproliferative disease. The term "treating" further is meant to include hydrating, healing or smoothing of the skin. The symptoms include but are not limited to growths, scaly skin, dry skin, rough skin, pustules and irritated skin. This treatment further includes prevention of these symptoms, and in particular scaly and irritated skin, before they occur.

As used herein, the phrase "dermatologically acceptable carrier" refers to a carrier or a diluent that does not cause significant irritation to the skin and does not abrogate the biological activity and properties of the applied active agent.

Examples of dermatologically acceptable carriers that are useful in the context of the present invention include, without limitation, emulsions, creams, aqueous solutions, oils, ointments, pastes, gels, lotions, milks, foams, suspensions and powders. Preferred carriers are the members of the polyethylene glycol (PEG) family of polymers.

The dermatologically acceptable carrier of the present invention may include, for example, a thickener, an emollient, an emulsifier, a humectant, a surfactant, a suspending agent, a film forming agent, a foam building agent, a preservative, an antifoaming agent, a fragrance, a lower monoalcoholic polyol, a high boiling point solvent, a propellant, a colorant, a pigment or mixtures thereof. A preferred surfactant is Steareth-20.

Therefore, the composition of the present invention may be, for example, in the form of an oil, a gel, a solid stick, a lotion, a cream, a milk, an aerosol, a spray, a foam, a mousse, an ointment or a fatty ointment or a powder.

The compositions of the present invention may be manufactured by processes well known in the art, e.g., by means of conventional mixing, dissolving, granulating, dragger-making, levigating, emulsifying, encapsulating, entrapping or lyophilizing processes.

The compositions for use in accordance with the present invention thus may be formulated in conventional manner using one or more physiologically acceptable carriers comprising excipients and auxiliaries, which facilitate processing of the active compounds into preparations which, can be used pharmaceutically.

Formulations

The compositions of the invention comprise a dermatologically or cosmetically acceptable carrier to act as a diluent, dispersant or vehicle for calcipotriol and nicotinamide, so as to facilitate their distribution when the composition is applied to the skin. Vehicles other than or in addition to water include liquid or solid emollients, solvents, humectants, thickeners and powders. The present invention may be formulated for topical administration in the form of aqueous or non-aqueous solutions, lotions, creams, gels, ointments, foam, mousse, sprays, emulsions, microemulsions, adhesive patches, powders and the like.

In one preferred embodiment, the composition of the invention is a mono-phase composition, i.e. a composition comprising a single solvent system, such as an ointment. Non-limiting examples of formulations are as follows:

Ointments

Ointments provide an effective method to apply active agents to the skin. In on embodiment the dermatological carrier comprises polyethylene glycol. In some embodiments a mixture of PEGs is preferred. In certain embodiments the dermal composition of the present invention has the following formulation:

about 10 µg/g to about 100 µg/g calcipotriol;
about 0.5 mg/g to about 25 mg/g nicotinamide;
about 70% to about 80% (w/w) PEG-400;
about 15% to about 25% (w/w) PEG-4000;
about 1% to about 5% (w/w) Steareth-20;
about 0.1 to about 1% (w/w) vitamin E.

In specific embodiments the present invention provides a dermal composition having the following formula:

50 µg/g calcipotriol;
2.1 mg/g nicotinamide;
77.7% (w/w) PEG-400;
20% (w/w) PEG-4000;
2% (w/w) Steareth-20;
0.3% (w/w) vitamin E.

In other specific embodiments the present invention provides a dermal ointment having the following composition:

10-50 µg/g calcipotriol;
2.1 mg/g nicotinamide;
77.7% (w/w) PEG-400;
20% (w/w) PEG-4000;
2% (w/w) Steareth-20;
0.3% (w/w) vitamin E.

Other dermal ointment compositions can be based on petrolatum and have the following composition:

about 10 µg/g to about 100 µg/g calcipotriol; about 0.5 mg/g to about 25 mg/g nicotinamide; about 35% to about 60% (w/w) petrolatum; about 35% to about 55% (w/w) mineral oil; about 1% to about 10% (w/w) Steareth-2; about 0.1 to about 1% (w/w) vitamin E.

In one aspect the present invention provides a composition comprising calcipotriol, wherein the calcipotriol does not significantly penetrate the skin. Skin permeation assays are known ion the art. One example is provided in Example 7, hereinbelow. In certain embodiments less than 10%, preferably less than 5% of the calcipotriol penetrates the skin. In some embodiments less than 3% and preferably less than 1% of the calcipotriol penetrates the skin. The composition comprises a PEG-based ointment comprises:

about 10 µg/g to about 100 µg/g calcipotriol;
about 70% to about 80% (w/w) PEG-400;
about 15% to about 25% (w/w) PEG-4000;
about 1% to about 5% (w/w) Steareth-20;
about 0.1 to about 1% (w/w) vitamin E.

In some preferred embodiments the composition is as follows:

about 20 µg/g to about 50 µg/g calcipotriol; about 77.7% (w/w) PEG-400; about 20% (w/w) PEG-4000; about 2% (w/w) Steareth-20; about 0.1 to about 1% (w/w) vitamin E.

Lotions and Creams

The composition of the present invention may be provided as a lotion or as a cream and may include at least one or more emollient, which can function as either or both a lubricating and thickening agent. The emollients can comprise in total from about 0.1% to about 50%, preferably from about 1% to about 10%, by weight of the composition. Any emollients known to those of skill in the art as suitable for application to human skin may be used. These include, but are not limited to: hydrocarbon oils and waxes, including mineral oil, petrolatum, paraffin, ceresin, ozokerite, microcrystalline wax, polyethylene, and perhydrosqualene; silicone oils; triglyceride fats and oils, including those derived from vegetable, animal and marine source; including jojoba oil and shea butter; acetoglyceride esters, such as acetylated monoglycerides; ethoxylated glycerides, such as ethoxylated glyceryl monostearate; fatty acids, fatty alcohols and derivatives thereof. Other suitable emollients include lanolin and lanolin derivatives; polyhydric alcohols and polyether derivatives; polyhydric alcohol esters; wax esters; vegetable waxes; phospholipids, such as lecithin and derivatives; sterols, including, but not limited to, cholesterol and cholesterol fatty acid esters; amides, such as fatty acid amides, ethoxylated fatty acid amides, and solid fatty acid alkanolamides.

The lotions may further contain from about 1% to about 10%, more preferably from 2% to 5%, of an emulsifier. The emulsifiers can be nonionic, anionic or cationic. Those with skill in the art may choose emulsifiers suitable for dermal compositions.

Other conventional components of such lotions and creams may be included. One such additive is a thickening agent at a level from 1% to 10% of the composition. Examples of suitable thickening agents include, but are not limited to: cross-linked carboxypolymethylene polymers, ethyl cellulose, polyethylene glycols, gum tragacanth, gum karaya, xanthan gums, bentonite and other clays, hydroxyethyl cellulose, and hydroxypropyl cellulose.

The lotions and creams are formulated by simply admixing all of the components together. Preferably calcipotriol dissolved, suspended or otherwise uniformly dispersed in the mixture.

Solutions and Suspensions

The solutions, which may be aqueous or non-aqueous, are formulated to contain an effective concentration each of the active agents, calcipotriol and NA.

Suitable organic materials useful as the solvent or a part of a solvent system are as follows: propylene glycol, polyethylene glycol, polypropylene glycol, glycerin, sorbitol esters, 1,2,6-hexanetriol, ethanol, isopropanol, diethyl tartrate, butanediol, and mixtures thereof. Such solvent systems can also contain water.

When the compositions of the invention are formulated as an emulsion, the proportion of the fatty phase may range from about 5% to about 80% by weight, and preferably from about 5% to about 50% by weight, relative to the total weight of the composition. Oils, emulsifiers and co-emulsifiers incorporated in the composition in emulsion form are selected from among those known to those with skill in the cosmetic or dermatological field.

Gels and Solids

Gel compositions can be formulated by simply admixing a suitable thickening agent to the previously described solution or suspension compositions. Examples of suitable thickening agents have been previously described with respect to the lotions.

The gelled compositions contain an effective concentration of the active agents; from about 5% to about 75% of an organic solvent as previously described; from about 0.5% to about 20% of a thickening agent, and the balance being water, another aqueous carrier or a combination of carriers.

Compositions of solid forms may be formulated as stick-type compositions intended for application to the skin. The solids also contain from about 50% to about 98% of the previously described emollients. This composition can further contain from about 1% to about 20%, of a suitable thickening agent, and, if desired or needed, emulsifiers and water or buffers. Thickening agents previously described with respect to lotions are suitably employed in the compositions in solid form.

Other ingredients, such as preservatives, including methyl-paraben or ethyl-paraben, perfumes, dyes or the like, that are known in the art to provide desirable stability, fragrance or color, or other desirable properties, to compositions for application to the skin.

The compositions formulated as solutions or suspensions may be applied directly to the skin, or, may be formulated as an aerosol and applied to the skin as a spray, foam or mousse. The aerosol compositions further contain from about 20% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as known in the art in a quantity and under a pressure suitable to expel the contents of the container. In the case of a pressurized aerosol, the dosage unit may be determined by providing a valve to deliver a metered amount.

In other embodiments the compositions formulated as solutions, suspensions lotions and gels of the present invention are formulated as a foam or mousse for dermal application. Relevant carriers for formulation as a foam or mousse are taught, for example, in International Patent Application Publication No. WO 2004/037225 and U.S. Pat. No. 6,730,288.

Dose

The compositions of the present invention are formulated for topical administration of the active ingredients up to four times daily. Preferably the formulation is therapeutically effective for a single daily administration.

Additives

The topical composition may additionally include a third or fourth pharmaceutically acceptable component. The invention also relates to a preferred pharmaceutical preparation according to the invention, which is especially useful for the treatment of hyperproliferative skin diseases which are complicated by additional fungal infections, and which further contains an anti-fungal agent. Non-limiting examples of an antifungal include miconazol, clotrimazol, terbinafin, ciclopirox, bifonazol, nystatin, ketoconazol, econazol, and amorolfine.

Other examples of additives include sunscreens. Sunscreens include those materials commonly employed to block ultraviolet light. Illustrative compounds are the derivatives of PABA, cinnamate and salicylate. For example, octyl methoxycinnamate (parsol MCX) and 2-hydroxy-4-methoxy benzophenone (also known as oxybenzone and benzophenone-3). The amount of sunscreen employed in the compositions can vary depending upon the degree of UV radiation protection desired. The sunscreen must be compatible with the active compound but in general the composition may comprise from about 1% to about 20%, of a sunscreen. Exact amounts will vary depending upon the sunscreen chosen and the desired Sun Protection Factor (SPF).

The composition of the present invention may further comprise an anti-oxidant. The inclusion of an anti-oxidant/radical scavenger may provide the composition with stability. The anti-oxidant/radical scavenger may be added to the compositions of the present invention in a concentration range of about 0.1% to about 10% total weight of the composition. Anti-oxidants/radical scavengers include ascorbic acid (vitamin C) and its salts, and tocopherol (vitamin E). A preferred additive is vitamin E. A certain preferred concentration range is about 0.1% to about 1%.

Other additives including glycosaminoglycans, such as hyaluronic acid and the like.

Methods of Treatment

The present invention further provides methods of preventing or treating a hyperproliferative skin disease or disorder comprising the step of:

topically administering to a subject in need thereof a therapeutically effective amount of a composition consisting essentially of calcipotriol at a concentration of about 10 µg/g to about 100 µg/g; nicotinamide at a concentration of about 0.1 mg/g to about 50 mg/g; and a dermatologically acceptable excipient or carrier.

The method comprises topical administration of the composition up to about four times daily. In preferred embodiments the composition is administered once or twice daily. In some embodiments the composition is applied twice daily at intervals of about 12 hours. In other embodiments the composition is administered once daily.

In some embodiments the method of treatment includes two treatment periods: an initial treatment, and a maintenance treatment.

Without wishing to be bound to theory, the initial treatment serves to reduce at least some of the signs and symptoms of the disease, while the second maintenance treatment serves to prevent the relapse or progression of the disease.

Accordingly, in the initial treatment a patient administers an initial dosage of the composition consisting essentially of calcipotriol at a concentration of about 10 µg/g to about 100 µg/g; nicotinamide at a concentration of about 0.1 mg/g to about 50 mg/g; and a dermatologically acceptable excipient or carrier for an initial period and thereafter, the patient administers a lower maintenance dosage of a composition consisting essentially of calcipotriol at a concentration of about 10 µg/g to about 50 µg/g; nicotinamide at a concentration of about 0.1 mg/g to about 50 mg/g; and a dermatologically acceptable excipient or carrier.

The initial dose of calcipotriol is preferably about 20 µg/g to about 70 µg/g, more preferably about 50 µg/g; the initial dose of NA is about 0.5 mg/g to about 25 mg/g, preferably about 1 mg/g to about 20 mg/g, and most preferably about 2.1 mg/g.

For the maintenance dosage, the calcipotriol is provided at a concentration of about 10 µg/g to about 50 µg/g. In some embodiments calcipotriol is provided at a concentration of about 15 µg/g to about 35 µg/g. In specific embodiments calcipotriol is provided at a concentration of about 30 µg/g. A maintenance dosage of NA is about 0.5 mg/g to about 25 mg/g. In certain embodiments nicotinamide is provided at a concentration of about 1 mg/g to about 20 mg/g. In other embodiments nicotinamide is provided at a concentration of about 2 mg/g to about 10 mg/gm, preferably at a concentration of about 2.1 mg/g.

According to certain preferred embodiments the present invention provides a method of preventing or treating a hyperproliferative skin disease or disorder comprising the steps of:

topically administering to a subject in need thereof a therapeutically effective amount of a composition consisting essentially of calcipotriol at a concentration of about 50 µg/g; nicotinamide at a concentration of about 2.1 mg/g; and a dermatologically acceptable excipient or carrier for an initial period of time to reduce the symptoms of the hyperproliferative disease, and topically administering to a subject in need thereof a therapeutically effective amount of a composition consisting essentially of calcipotriol at a concentration of about 15 µg/g to about 35 µg/g; nicotinamide at a concentration of about 2.1 mg/g; and a dermatologically acceptable excipient or carrier for a second period of time.

In one embodiment the initial treatment period is about 4 weeks to about 24 weeks, preferably from about 4 weeks to about 16 weeks. In certain preferred embodiments the initial treatment period is from about 6 weeks to about 12 weeks, preferably about 8 weeks. The second period of time is about 8 weeks to about 52 weeks, preferably from about 12 weeks to about 26 weeks.

Product Packaging and Kits

In use, a small quantity of the composition, for example from about 0.1 ml to about 100 ml, is applied to exposed areas of the skin, from a suitable container or applicator and, if necessary, it is then spread over and/or rubbed into the skin using the hand, fingers or a suitable device. The product may be specifically formulated for use as a hand or facial treatment.

When formulated the composition can be packaged in a suitable container to suit its viscosity and intended use by the consumer. For example, an ointment can be packaged in a tube, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a dermatologically or cosmetically acceptable composition as herein defined. The shape of the container is not limited in this invention, and can be a tube, a pump dispenser, a compressed dispenser, a bottle, a spray, a sachet or the like.

Many of the agents in the claimed compositions of the present invention may be provided as physiologically acceptable salts wherein the agent may form the negatively or the positively charged species. Examples of salts in which the agent forms the positively charged moiety include, without limitation, quaternary ammonium salts such as the hydrochloride, sulfate, carbonate, lactate, tartrate, maleate, succinate, and the like, wherein the nitrogen of the quaternary ammonium group is a nitrogen of a compound of the present invention which reacts with an appropriate acid. Salts in which the agent forms the negatively charged species include, without limitation, the sodium, potassium, calcium and magnesium salts formed by the reaction of a carboxylic acid group in the molecule with the appropriate base (e.g., sodium hydroxide (NaOH), potassium hydroxide (KOH), calcium hydroxide ($Ca(OH)_2$) etc.).

The compositions of the present invention may, if desired, be presented in a pack or dispenser device, such as a regulatory agency approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of the compositions, which notice is reflective of approval by the agency of the form of the compositions or human or veterinary administration. In other embodiments the compositions are prepared for over the counter (OTC) use and sale.

Compositions comprising the agents of the invention formulated in a compatible carrier may also be prepared, placed in an appropriate container, and labeled for prevention and treatment of a skin disorders associated with aging.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

The following examples are to be considered merely as illustrative and non-limiting in nature. It will be apparent to one skilled in the art to which the present invention pertains that many modifications, permutations, and variations may be made without departing from the scope of the invention.

The in vitro and in vivo data that have provided the basis for the composition of the present example are as follows:

Example 1

In vitro Experiments

Certain in vitro assays based on keratinocyte cell culture were performed to test NA and the combination of NA and calcipotriol. The experimental design has been described in PCT Patent Publication WO 01/51051, of some of the inventors of the present application.

The results of the in vitro studies indicate that:

Proliferation of all cell lines (HaCat keratinocytes, human primary keratinocytes, A431, KM12) was significantly inhibited by NA in pharmacological concentrations, in a dose dependent manner;

A combination of NA with calcipotriol provides a synergetic antiproliferative effect;

NA promotes the differentiation processes in benign and malignant epidermal cells as shown by increased expression of early (K10), late (Involucrin) and terminal (enveloped cornified cell formation) differentiation markers;

NA does not induce apoptotic death in HaCat and A431 cells; and

Long-term treatment of HaCat keratinocytes with NA demonstrated a high level of protection to oxidative stress (hydrogen peroxide) and high levels of anti-oxidative enzymes (glutathione peroxidase and catalase).

The experiments and their results are summarized herein below:

Cell Culture

The antiproliferative activity of calcipotriol and nicotinamide was tested in two model systems: the first a spontaneously immortalized human keratinocyte, which is referred to herein as "HaCat cells" or "HaCat keratinocytes", and serves as a model for highly proliferative epidermis, such as, but not limited to, psoriatic epidermis (Okenfels et al, 1998), and as a model for effects of external modulators of epidermal differentiation (Paramio, et al., 1997). The second system includes rapidly proliferating human keratinocytes, which are referred to herein as "cultured human epidermal keratinocytes", and serves as a model for detecting antiproliferative agents in the treatment of psoriasis (Nikoloff, et al., 1988).

These models have been used, according to the present invention, to test the antiproliferative efficacy of agents described herein. The immortalized human keratinocyte HaCat cells are routinely cultured in 75 cm² flasks using Eagle's minimal essential medium (MEM-EAGLE) supplemented with 5% fetal calf serum (FCS) and 1% antibiotics (penicillin 20 units/ml; streptomycin 20 µg/ml and nystatin 2.5 units/ml) at 37° C. in 95% air/5% $CO_2$. The medium is replaced every 3-4 days.

Long-term cultures of HaCat cells grown with calcipotriol were obtained by cultivating HaCat cells, for 6 months, in routinely used medium.

Other long-term cultures of cells with other agents are similarly obtained by cultivating HaCat cells, for a prolonged period of time, in medium supplemented with combinations of NA, vitamin D and derivatives thereof and vitamin A.

Human Epidermal Keratinocytes (passages 3-6), obtained from normal face-lift surgery, were cultivated in serum-free KGM®-2 BulletKit® (Clonetics, USA) medium with low calcium for accelerated proliferation of the keratinocytes.

Reagents:

Nicotinamide (NA); calcitriol (1α, 25-dihyroxy-vitamin D3); 3-(4,5-dimethylthiazol-2-yl)-2,5-diphenyltetrazolium bromide (MTT); propidium iodide; dimethylsulphoxide (DMSO); bovine serum albumin (BSA); sucrose; trisodium citrate; igepal CA-630 (NP-40); Tris-(hydroxymethyl)-aminomethane; trypsin; trypsin inhibitor; ribonuclease A; spermin-tetrahydrochloride; sodium dodecylsulfate (SDS); β-mercaptoethanol and hydrogen peroxide ($H_2O_2$), were all obtained from Sigma (USA).

Eagle's minimal essential medium (MEM-EAGLE), DMEM; antibiotics; fetal calf serum (FCS); L-glutamine; Dulbecco's phosphate buffered saline (PBS); and trypsin 0.05%-EDTA solution were obtained from Biological Industries (Israel).

Keratinocyte Growth Medium®-2 Bullet Kit® CC-3107 (for accelerated proliferation) was received from BioWhittaker, Inc. (Clonetics, USA).

Anti-human cytokeratin 10 (NCL-CK10) and involucrin (NCL-INV) mouse monoclonal antibodies were obtained from Novocastra Laboratories Ltd. (UK) and Cy™ 2-conjugated goat anti-mouse IgG was obtained from Jackson Immunoresearch Laboratories, Inc. (USA).

HaCat cells were propagated in 25 cm² or 75 cm² tissue culture flasks (Corning, USA) and 24-well and 96-well tissue culture plates (Corning, USA) were used for incubation of the cells with different doses of NA (1-50 mM/l) and calcipotriol (1-10000 nM).

Proliferation Assays (MTT Method)

The viability and/or proliferation of HaCat cells and Cultured Human Epidermal Keratinocytes, following treatment with various concentrations of calcipotriol, nicotinamide (NA) or a combination thereof was determined by the MTT assay, according manufacturer in 96-well microtiter plates.

Apoptosis and Mitotic Activity Assays

Estimation of apoptosis and necrosis was analyzed using fluorescence microscopy as previously described (Harel et al, 2002). Briefly, HaCat cells were cultured on glass slides and exposed to various concentration of NA (5, 10, 20 and 50 mM). After 72 h the cells were stained with the DNA binding dyes Hoechst 33342 and propidium iodide. Viable cells were identified by intact nuclei and their blue fluorescence, necrotic cells by intact nuclei and red fluorescence, and cells in early or late phase of apoptosis, by fragmented nuclei and blue or red fluorescence. At least one thousand cells were counted for each treatment.

Determination of apoptosis and cell cycle parameters was performed by flow cytometry. Cells were seeded in 25 cm2 tissue culture flasks and cultured for 48 h, and then they were exposed to 5, 10 and 20 mM NA for 72 h. Flow cytometry was performed on nuclei prepared with a detergent-trypsin method and stained with propidium iodide (Vindelov et al, 1983).

Immunoblot analysis of PARP expression: immune complexes were detected by incubation with secondary anti-mouse alkaline phosphatase conjugated antibody AP124A (dilution 1:5000) followed by developing with BCIP/NBT color substrate.

Growth curve and mitotic activity: $2 \times 10^4$ cells per ml were seeded in 24-well tissue culture plates and incubated without or with 10 mM NA. The cells were detached by trypsinization at different times (48 h-168 h) following passage and counted using a haemocytometer in tetra-aliquots. For estimation of mitotic activity the cells were cultured on glass coverslips into Petri dishes. After 72 h incubation with or without 10 mM NA the cells were fixed with methanol, stained with Giemsa stain and analyzed by light microscopy. Frequency of mitotic cells at different stages of mitotic cycle (pro-, meta-, ana- and telophases) was calculated. At least 1000 cells were counted for each experiment.

Differentiation Assays

Cornified Envelope Formation: Late differentiation processes in HaCat cells treated with NA and or calcipotriol were measured by determining the cornified cell envelope formation, according to the procedures described in Sun and Green (1976) and PCT publication WO 01/51051.

Indirect Immunofluorescence:

Effects of NA and or calcipotriol on early (keratin k10 expression) and late (involucrin expression) differentiation processes in HaCat cells were estimated by indirect immunofluorescence.

In brief, $2 \times 10^4$ cells/ml were seeded on glass coverslips into Petri dishes with 0, 5, 10 and 20 mM NA or calcipotriol. After 72 hours of incubation, cells on the glass coverslips were washed with PBS, fixed by ice-cold mixture of methanol:acetone (1:1) and incubated at −20° C. for 10 minutes. Fixed cells were washed in PBS and incubated with blocking buffer (1% BSA in PBS) for 10 minutes, to minimize non-specific absorption of the primary antibodies to the coverslips. Thereafter, the cells were incubated for 1 hour with primary monoclonal antibodies (Keratin 10 expression was detected by antihuman mouse monoclonal antibody, at 1/50 final dilution; Involucrin expression was detected by antihuman involucrin mouse monoclonal antibody at 1/100 final dilution), at 37° C. hour in a humidified chamber. Exhaustive, PBS-washed cells were incubated with fluorophore conjugated goat anti-mouse IgG, at 1/50 final dilution, for 30 minutes at room temperature. The slides were viewed under a Zeiss microscope (Axioskop-2) equipped with epifluorescence optics and the appropriate filters to avoid cross-channel contamination. The level of keratin 10 and involucrin expression was estimated by counting the positive cells relative to the total cell number. On each slide, at least 500-1000 cells were scored.

Statistical Analysis

Results are presented as mean±standard deviation of the mean (mean±SD). Statistical significance ($P<0.05$) was derived by Student's t-test.

Results

NA inhibited HaCat cell proliferation in a dose-dependent manner. Incubation for 72 h with low doses of NA (0.5-5 mM) did not change the rate of HaCat cell proliferation. However, higher concentrations of NA markedly reduced the proliferative response in dose-dependent manner. A pharmacological concentration of about 10 mM, resulting in two-fold inhibition of cell proliferation, was chosen for studying effect of NA on HaCat cell mitotic activity, growth curve and cell cycle progression. Microscopic analysis of mitotic activity indicated that percentage of mitotic cells was about 2.5 times lower in population of NA treated cells compared to untreated ones. Similar results of growth retardation were obtained after incubating HaCat cells with 10 mM NA for 48-168 hours.

In order to elucidate the perturbation in cell cycle that can lead to growth retardation induced by NA treatment, frequency of cells in G0-G1, S and G2-M phases was studied by flow cytometry analysis. An inverse correlation between progression of the cells through G0-G1 phase of cell cycle and reduction of the cell number in S and G2-M-phases after incubation with NA for 72 h in dose dependent manner was shown.

NA induces apoptosis, but not necrosis in HaCat cells. Using fluorescence microscopy, an estimate of apoptosis and necrosis could be made in a single sample. The levels of spontaneous apoptosis and necrosis in intact HaCat cells were 0.8±0.22% and 0.3±0.1%, respectively. Nicotinamide concentrations of 20 mM and 50 mM display significant apoptogenic effect in HaCat keratinocytes. At 50 mM of NA about 91% of effected cells displayed signs of late apoptosis (red condensed and fragmented nuclei) and only 9% of the cells were in stage of early apoptosis (blue condensed and fragmented nuclei). However, no tested concentration of NA induced necrotic cell death. Thus, NA is a good candidate for the treatment of dermal disorders.

Data on the Western blot analysis demonstrate that intact HaCat cells and the cells treated with 10 mM or 20 mM NA express a basal level of undegraded 116 kDa PARP full protein. However, an NA dose of 50 mM induced degradation of PARP and appearance of 85 kDa cleavage fragment of PARP. Terminal differentiation of keratinocytes was estimated by the level of cornified envelope cell formation, which reflects protein-protein cross-linking reaction catalyzed by transglutaminase on the cytoplasmic side of the plasma membrane (Steinert and Marekov, 1997). The majority of untreated HaCat cells consisted of nonmaturated basal cells (58.6±10.24%), while differentiated cornified envelope cells constituted only 4.4±2.78% of total cell number. Incubation of the cells with 5 mM NA or 10 mM NA had no statistically significant effect on frequency of both basal and cornified envelope cells. When concentrations of NA were increased to 15 mM, the level of basal cells was greatly reduced to 25.6±5.76%. At this concentration of NA cornified envelope cell formation increased. Further reduction of basal cell number and elevation of envelope cornified cell formation was found at 20 mM NA. At this concentration of NA the frequency of both basal and envelope cornified cells was identical and equal about 15% of total cell population.

To estimate differentiation-promoting processes foregoing the cornified envelope cell formation, the level of keratin 10 (K10) and involucrin expression was determined. A concentration of 20 mM NA caused an increase in expression of keratin10 and involucrin in HaCat keratinocytes. The quantitative analysis indicates that NA in concentrations from 5 mM to 10 mM had no effect on K10 expression compared to control cells. However, higher concentration of NA (20 mM) induced 3-fold stimulation of K10 expression in HaCat cells. In contrast to K10, the involucrin expression was significantly more sensitive to NA treatment. The level of involucrin expression in HaCat cells treated with 5 mM NA was increased about 2 times (11.2±1.68% vs. 6.0±1.22% in control). The enhanced frequency of involucrin positive cells was found at 10 mM and 20 mM (11.0±1.13% and 15.1±3.93% respectively). These results show that NA treatment stimulates expression of various differentiation markers of HaCat cells in dose-dependent fashion.

In conclusion, both the fact that pharmacological doses of NA are a safe therapy and above mentioned data on antiproliferative and differentiation promoting effect of this vitamin on human epidermal HaCat keratinocytes suggests a strong therapeutic potential of NA for treatment of different hyperproliferative skin disorders.

Example 2

Formulation Development Strategy

The formulation development strategy was based on the following principles:
a) Formulations with wide diversity in composition;
b) Use of pharmaceutical grade, approved ingredients;
c) Determine accelerated stability at 40° C. and potency measured in the mouse-tail model, compared to commercially available compositions;
d) Optimization of the concentration of the active ingredients, based on activity measured by the mouse-tail model.

Preparation of Ointment Formulations

Eight distinct base formulations were prepared. Formulations 1-4 and 8 were a petroleum gel/mineral oil base; formulation 5 was a PEG base; formulation 6 was a triglyceride-water base; formulation 7 was a triglyceride-glycerin base. To the base formulations (numbered 1 to 8) 50 μg/g of calcipotriol and 0.61 mg/g of nicotinamide were added. About 300 gr of each formulation was prepared. These preparations were used for the analytical method development (extraction), accelerated stability at 40° C. and biological activity assessment (potency).

Calcipothiol Determination (HPLC Method)

This method was used to determine the Calcipotriol content in Calcipotriol-Nicotinamide ointment formulations using HPLC with UV detection.

Materials: All materials: analytical grade; all solvents: HPLC grade

Calcipotriol standard (5.0 μg/ml calcipotriol)
Methanol
Acetonitrile
HPLC Conditions:
Hypersil® ODS-2, 5 μm, 250×4.6 mm column.
Guard column: Opti-Guard®, C18, 1 mm.
Mobile phase: 60% Acetonitrile in water
Preparation of mobile phase: For every liter of mobile phase mix well 600 ml of Acetonitrile and 400 ml of water.
Diluent: 90% Methanol in water
Flow rate: 1 ml/min; Sample volume: 50 μl; Detector: UV 264 nm; Column temperature: 25° C.; Autosampler temperature: 25° C.—controlled temperature; Run time: 12 minutes.

Calculations: Calcipotriol content in the formulations was calculated from the ratio between the peak area of sample to the average peak area of all working standard solution injections.

Nicotinamide Determination (HPLC Method)

This method is intended for the determination of nicotinamide (niacinamide) content in calcipotriol-nicotinamide cream formulations using HPLC with UV detection.

Materials:
Nicotinamide standard (24 μg/ml)
Potassium dihydrogen phosphate ($KH_2PO_4$)
Potassium hydroxide (KOH)
Acetonitrile
Water HPLC Conditions:

Column & packing: Grom-Sil 120 ODS-5ST, 5 μm, 150×4 mm, or equivalent.

Guard column: Opti-Guard®, C18, 1 mm.

Mobile phase: Eluent A: 3% Acetonitrile in phosphate buffer (pH 6.6), Eluent B: 50% Acetonitrile in phosphate buffer (pH 6.6)

Flow rate: 0.8 ml/min; Injection volume: 20 μL; Detector: UV 261 nm; Column temperature: 30° C.; Autosampler temperature: about 20° C.; Run time: 9 min for standard solutions, 23 min for sample solutions.

Calculations: Nicotinamide content in formulation was calculated from the ratio between the peak area of sample to the average peak area of all working standard solution injections.

Method of Extraction of Formulated Calcipotriol & Nicotinamide

Calcipotriol Extraction from Formulations

Formulations 1, 2, 4, 5, 6, 7 were treated as follows:

1. About one gram of sample was weighed into a 20 ml glass vial, 10 ml of the diluent (methanol:water 9:1 V/V) was added, vortexed for 1 min and left to stand for 5 min.

2. About 1 ml of the resulting mixture was transferred into a centrifuge tube with 0.22 mm filter and centrifuged for 5 min at 13000 rpm.

3. The collected filtrate was injected on HPLC.

Formulations 3, 8 were treated as follows:

1. About one gram of sample was weighed into a 20 ml glass vial, 10 ml of the diluent (methanol:water 9:1 V/V) was added and vortexed for 1 min.

2. Sonication for 10 min with periodical vigorous shaking was performed.

3. Mixing by vortex for about 1 min was performed.

4. About 1 ml of the resulting mixture was transferred into a centrifuge tube with 0.22 mm filter and centrifuged for 5 min at 13000 rpm.

5. The collected filtrate was injected on HPLC.

Nicotinamide Extraction from Formulations

Formulations 2, 4, 5, 6, 7 were treated as follows:

1. About one gram of sample was weighed into a 25 ml volumetric flask, dissolved by mixing and brought up to volume with water.

2. Sonication with periodical vigorous shaking was performed for 10 min.

3. About 1 ml of the resulting mixture was transferred into a centrifuge tube with 0.22 mm filter and centrifuged for 5 min at 13000 rpm.

4. The collected filtrate was injected on HPLC.

Formulations 1, 3, 8 were treated as follows:

1. About one gram of sample was weighed into a 50 ml glass bottle, 25 ml of water were added and mixed by vortex for 30 sec followed by sonication at 40° C. for 30 min with periodical vigorous shaking.

2. Then the resulting mixture was allowed to cool at ambient temperature and filtrated through 0.45 mm filter.

The filtrate was injected on HPLC.

Results: Formulations 1, 2 and 5 were found to be the most stable, after exposure to 40° C. for 60 days (greater than 85% recovery of calcipotriol and NA). Formulation 5 remained the most stable even after 180-day exposure.

Example 3

Potency Evaluation

Potency evaluation assay were performed with formulations 1, 2 and 5. The Potency evaluation was performed according to the procedure published in Bosman B., et al. (1992) with the following modifications:

Collars were placed on the mice to prevent licking rather than mounting a tub on the treated area; and male albino mice (ICR) were used instead of male albino mice (NMRI) with same weight and age.

Figure 1B:
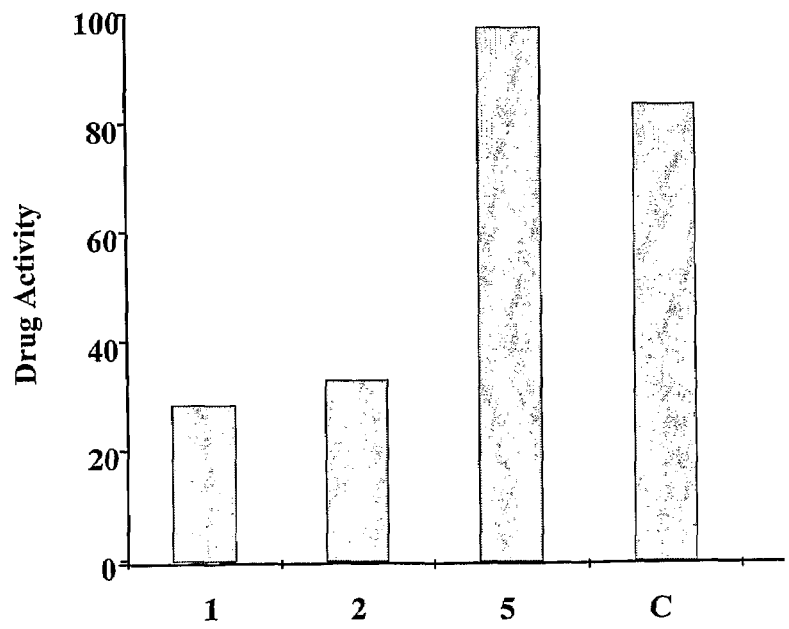

Two experiments were performed: the first assay was carried out to test the relative potency of the different base compositions comprising 50 μg/g calcipotriol and 0.61 mg/g. Since formulas 1, 2 and 5 were found to be the most stable, i.e. the active ingredients remain stable after 60 days at 40° C. The results of this experiment are presented in FIGS. 1A (% orthokeratosis) and FIG. 1B (% activity of active ingredients). The letter "V" refers to the vehicle alone, and V-1; V-2 and V-5 refer to the vehicles of compositions 1, 2, and 5, respectively. The numbers 1, 2 and 5 refer to formulations 1, 2 and 5 respectively.

The second assay related to optimizing the nicotinamide concentrations in the compositions. Accordingly, six different compositions were screened for their potency, using a concentration of 50 μg calcipotriol and 3-fold increasing nicotinamide concentrations starting with 0.70 mg/g formulation. These formulations were compared to a commercially available composition comprising 50 μg/g calcipotriol.

The experimental outline is presented herein below in Table 1. The results of orthokeratosis are presented in Table 2 herein below.

TABLE 1

| Description | Duration |
|---|---|
| Number of formulations tested: 5 + 1 active control | 7 days |
| I: 50 μg/g calcipotriol and 0.70 mg/g nicotinamide | |
| II: 50 μg/g calcipotriol and 2.1 mg/g nicotinamide | |
| III: 50 μg/g calcipotriol and 6.3 mg/g nicotinamide | |
| IV: 50 μg/g calcipotriol and 18.9 mg/g nicotinamide | |
| Veh: Vehicle | |
| C: (Control) commercially available calcipotriol composition (Daivonex ®) | |
| Mice - Male albino mice (ICR) weighting 25-27 g 6 mice per formulation. control: 6 mice Total 36 mice (5 × 6 + 6 = 36) | |
| Treatments: 6 treatments per week for 7 days | 7 days |
| Treatment: Topical application once a day on the tail base: about 1 cm from the proximal end of the tail to about 2.5 cm section long, for 3.5 hours. Treatment area was rinsed with saline. During the treatment, the tail was protected from licking by mounting collars on the mice chests. | |
| At the end of experiment the mice were sacrificed. The treated section of tail, ~2.5 cm was removed and fixed in 4% formalin. Longitudinal histological sections from the treated tail were prepared at Pathology Department. 10 sections/tail. Evaluation of % orthokeratosis performed by Dermatology laboratory. | On day 7 |

TABLE 2

| Formulation | % Orthokeratosis/Scale |
|---|---|
| Vehicle (PEG based ointment) | 24.1 ± 7.3 |
| Active Control (Commercially available) | 35.4 ± 14.2 |
| 50 μg Calcipotriol & 0.7 mg/g Nicotinamide | 47.4 ± 12.5 |
| 50 μg Calcipotriol & 2.1 mg/g Nicotinamide | 94.3 ± 14.1 |
| 50 μg Calcipotriol & 6.3 mg/g Nicotinamide | 77.4 ± 22.3 |
| 50 μg Calcipotriol & 18.9 mg/g Nicotinamide | 65.4 ± 27.0 |

Figure 2A:
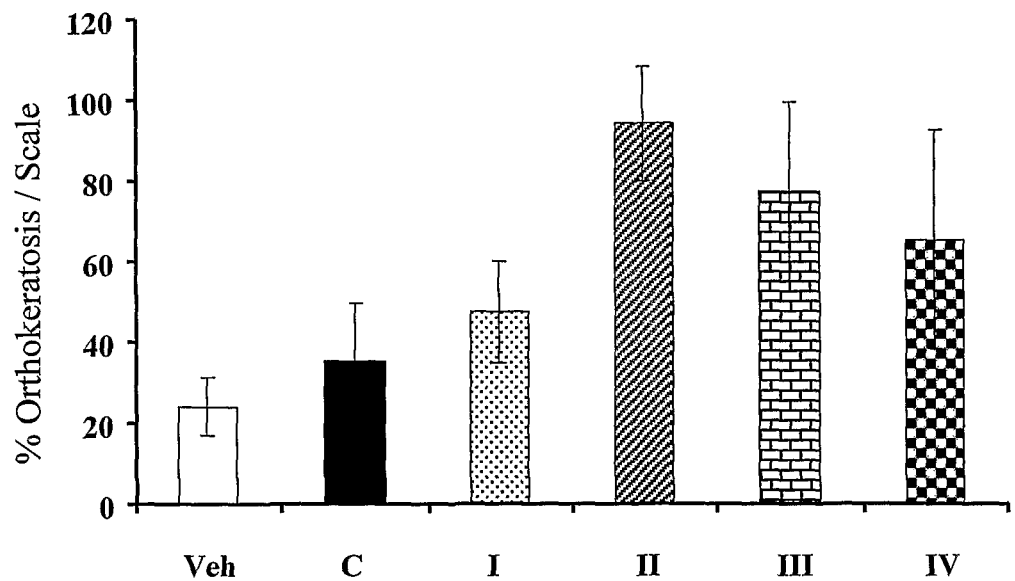
FIGS. 2A-2B.

FIG. 2A is a graph showing the levels of orthokeratosis induced in mice tails by the various compositions of the invention. Specifically, optimization of the NA concentration in a composition comprising 50 μg/g calcipotriol, was shown.

Figure 2B:
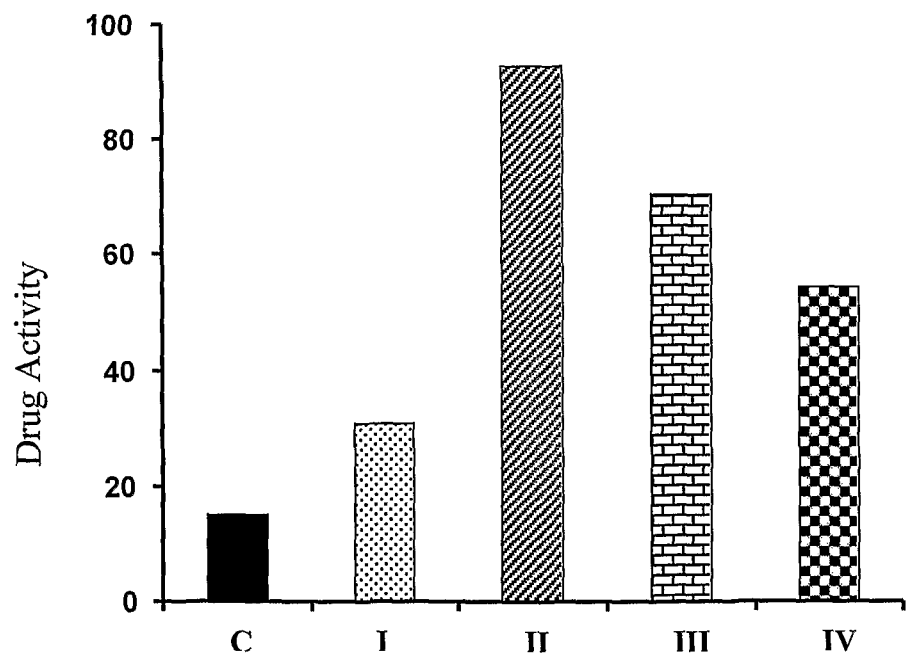

FIG. 2B shows the level of drug activity in the different formulations according to the present invention.

Both graphs show that the compositions including 50 µg/g calcipotriol and all tested concentrations of NA performed better than a commercially available (Daivonex) composition of 50 µg/g calcipotriol. The best results were obtained by a composition of 50 µg/g calcipotriol and 2.1 mg/g NA (II). Roman numerals I, II, II and IV refer to compositions of 50 µg/g calcipotriol and either 0.7 mg/g (I); 2.1 mg/g (II); 6.3 mg/g (III) or 18.9 mg/g (IV) nicotinamide.

Example 4

Formulations

Method for Preparing the Drug Formulation

Calcipotriol was dissolved in propylene glycol (PG). The 5% w/w calcipotriol solution was mixed with 95% w/w PEG-based base formulation. Nicotinamide was added either to the calcipotriol solution directly or together with Vitamin E to the melted mixture of PEG-4000 and Steareth-20 in PEG-400 at precisely 45° C. to reach a final concentration of 2.1 mg NA/g formulation.

Table 3 shows a PEG-based base formulation of the invention.

TABLE 3

| Base Formulation | |
|---|---|
| Ingredients | % W/W |
| Vitamin E | 0.30 |
| Steareth 20 (Lipocol S20) | 2.00 |
| PEG-400 | 77.70 |
| PEG-4000 | 20.00 |
| Total | 100.00 |

Detailed Methods of Preparation

One (1) mg calcipotriol was added to one ml of PG in a 40° C. water bath with slight mixing until all calcipotriol dissolved and no crystals were observed. This solution is suitable for a 20 g preparation (final conc. 50 µg/gr).

PEG-4000 and Steareth-20 in PEG-400 were melted together in a water bath (~60° C.) and mixed well to homogeneity. The mixture was cooled to below 50° C.

Vitamin E and calcipotriol/PG was added to the PEG-4000 and Steareth-20 in PEG-400 mixture at a ratio of 5% w/w CP solution in PG with 95% w/w mixture.

Alternatively, nicotinamide may be added with the Vitamin E: 42.0 mg NA for 20 g preparation (final conc. NA 2.1 mg/gr), or can be dissolved in the calcipotriol solution.

The mixture was well blended and tubes were filled.

Example 5

Synergistic Effect of Calcipotriol and NA in vivo

The in vivo studies aimed to measure antipsoriatic activity (potency) of the compositions comprising NA and calcipotriol utilizing the standard mouse-tail test (see Example 3). The induction of a granular layer (orthokeratosis or normal maturation) in scale areas of mouse-tail skin and/or abnormal maturation (parakeratosis) is a relevant parameter for antipsoriatic activity.

The test was performed large scale, with 100 measurements each for Placebo (PL), Calcipotriol (CP) 50 µg/gr and a mixture pf Calcipotriol and Nicotinamide (CPNA). 90 measurements were obtained for Nicotinamide (NA) 2.1 mg/gr.

All mice participating were randomized before evaluation and treatments were reassigned to data points only after microscopic analysis was complete in a fully blinded procedure.

Treatments were analyzed using an ANOVA procedure for all treatments. Treatment with CP or NA alone provided good results but treatment with CPNA was significantly better, indicating a synergistic effect of CP and NA.

The means and their standard deviations obtained are given below in Table 4:

TABLE 4

| Treatment | Mean | Standard Deviation |
|---|---|---|
| PL (placebo) | 0.3030 | 0.0085 |
| CP | 0.4449 | 0.0085 |
| NA | 0.4651 | 0.0090 |
| CPNA | 0.9596 | 0.0085 |

For single dose points per treatment it was possible to evaluate an estimate S of the synergistic effect by means of calculating a ratio of the results of the combined treatment to a sum of the separate treatments, where all treatments are adjusted by subtracting the placebo result from each of the separate results, as in the following equation: $S=(CPNA-PL)/\{[(CP-PL)+(NA-PL)]\}$ The value S was estimated to be 2.16 with an estimate of its standard error: 0.0211. It is therefore clear that synergism exists between CP and NA for the conditions of the performed test.

Table 5 herein below shows the results of this evaluation.

TABLE 5

| Formulation | % Orthokeratosis/Scale |
|---|---|
| Placebo (PL) (Vehicle) | 30.3 ± 4.4 |
| Calcipotriol (CP) 50 µg/g | 44.5 ± 6.1 |
| Nicotinamide (NA) 2.1 mg/g | 46.5 ± 9.2 |
| Combined (CP + NA) | 96.0 ± 10.6 |

Figure 3:
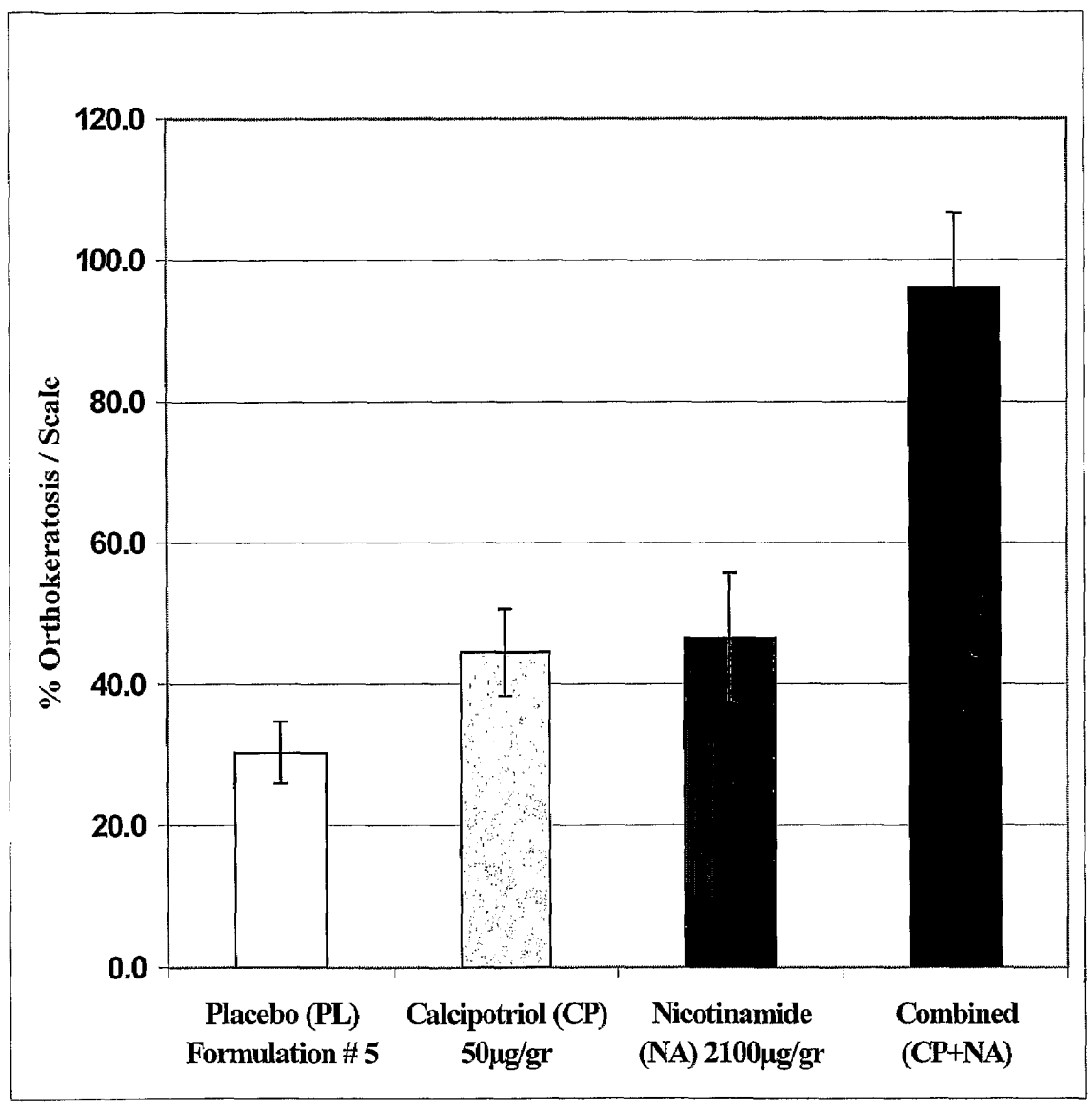
FIG. 3 shows the synergistic effect of CP and NA as an increase in orthokeratosis.

FIG. 3 is a graph that depicts the results of the above analysis. The synergistic effect of calcipotriol and nicotinamide at the above-mentioned concentrations is evident (Combined, (CP+NA)).

Example 6

Acute Dermal Irritation/Corrosion in Rabbits

This study was conducted to comply with: OECD Principles of Good Laboratory Practice (as revised in 1997); OECD Environmental Health and Safety Publications Series on Principles of Good Laboratory Practice and Compliance Monitoring—Number 1. ENV/MC/CHEM (98) 17; OECD Guideline for the Testing of Chemicals, Section 4, No. 404, "Acute Dermal Irritation/Corrosion", adopted Apr. 24, 2002; and ISO 10993-10:2002 (E) Second Edition 1 Sep. 2002, Biological Evaluation of Medical Devices-Part 10: Tests for Irritation and Delayed-Type Hypersensitivity. Section 6.3 Animal Skin Irritation Test.

Objective: Assessment of the potential of the Test Items to produce dermal irritation/corrosion by single dose application to the rabbit, thereby providing information on possible health hazards likely to arise from exposure of the skin to the test substance under conditions of its projected use as a therapeutic agent for Psoriasis.

Test material: Calcipotriol+nicotinamide (NA) in the following concentrations: 50 microgram/gram calcipotriol, 2.1 milligram/gram NA in an PEG base.

Test system: Rabbit/New Zealand White (NZW) Female, about 3-4 months old, about 2 kg at study commencement. The animals are acclimated for at least 5 days. A veterinarian examined the health status of the animals used in this study on arrival. Only animals in good health are acclimatized to laboratory conditions and used in the study.

Housing: Rabbits were housed individually in stainless steel cages mounted in batteries. The cages measured 60 (L)×50 (W)×45 (H) cm plus a shelf sized about 50 (L)×20 (W) cm placed about 20 cm above the cage floor. Rabbits were fitted with perforated plastic floors over under trays.

Food and Water: Animals were provided with approximately 100 g/rabbit/day commercial rabbit diet and allowed free access to drinking water, supplied to each cage via polyethylene bottles with stainless steel sipper tubes. The water was filtered (0.1 µ filter), chlorinated and acidified and is monitored for contaminants twice yearly.

Environment: Automatically controlled environmental conditions were set to maintain temperature at 17-23° C. with a relative humidity (RH) of 30-70%, a 12-hr light/12-hr dark cycle and 15-30 air changes/hr in the study room. Temperature and RH were monitored daily. The light cycle was monitored by the control computer.

Identification: Animals were identified by the breeder by a tattoo or by a marking dye ear number. This number also appears on a cage card, visible on the front of each cage. The cage card additionally contained the study number and relevant details as to treatment group and dose level.

Termination: Rabbits were euthanized by an IV overdose of Na-Pentobarbital (75 mg/kg), at any time that an animal shows continuing signs of severe pain or distress or in case where histopathological examination is required to clarify equivocal responses.

Justification: The albino rabbit was selected for this study, as it is the species of choice specified by the OECD and EPA Guidelines for use in dermal irritation/corrosion testing.

Dose: 0.5 g/animal

Test procedures:

Principles of the Test: The sequential method applied in this study represents a stepwise procedure aimed to avoid the unnecessary use of animals. The test was performed initially using one animal. Depending upon the results, a confirmatory test using additional animals was performed. The Test Item was applied in a single dose to the skin of the test animal. Adjacent areas of untreated skin of each animal served as a control. The degree of irritation/corrosion is evaluated and scored at specific intervals.

Pre-Test Preparations of Animals: Approximately 24 hours before the test, the fur was removed by close-clipping the dorsal area of the trunk of the animals using an electric clipper. Care was taken to avoid abrading the skin and only animals with healthy intact skin are used. In case areas of dense hair growth was observed, those are not used as test sites.

Application of the Test Item: The Test Item was applied either directly to the skin, or to a gauze patch (approximately 6 cm$^2$), which was then applied immediately and directly to the skin. The patch was held in contact with the skin with a non-irritating tape and a suitable semi-occlusive dressing (TUBIGRIP stockinet) to retain the gauze patch and the Test Item throughout the 4-hour exposure period and to ensure that the animal cannot ingest the Test Item. The untreated skin area of each animal serves as control. Test Item was applied sequentially as follows:

Initial Test: A single patch was applied to one animal for 4 hours. (If dermal corrosion would have been noted, the study would have immediately been terminated).

Confirmatory Test: Was not necessary. If an irritant effect would have been observed in the initial test, the confirmatory test would have been conducted in a sequential manner or by exposure of two additional animals simultaneously. Exposure Periods and Removal of Patches: At the end of the 4-hour exposure period, residual Test Item was removed using tap water or an appropriate solvent without altering the existing response or the integrity of the epidermis. The margins of the test site were marked with non-irritating and non-erasable ink in order to facilitate the subsequent observation sessions.

Analgesia: An opioid analgesic may be used on a case-by-case basis in view of animal welfare considerations for the use of laboratory animals in research.

Observations:

Observation Period: The duration of the observation period should be sufficient to evaluate fully the magnitude and reversibility of the effects observed. However, the experiment would have been terminated at any time that the animal shows continuing signs of severe pain or distress. Animals that do not develop skin lesions are observed for a period of 72 hours following removal of the patches. Further observations may be needed to establish reversibility up to 14 days post application. In case of extended observation period beyond 72 hrs, each animal is observed until reversibility is seen, or up to a maximum of 14 days.

Clinical Observations and Grading of Skin Reactions: All animals were examined for signs of erythema and edema, and the responses are scored at 1, 24, 48, and 72 hours after patch removal. For the initial test in one animal, the test site was also examined immediately after the patch has been removed. If animals were observed for up to 14 days, further examinations are performed once daily following removal of patch in order to determine the status of the lesions, and their reversibility. The grades of skin reactions were recorded at each examination.

Any dermal reactions other than those listed (e.g. limited area alopecia, hyperkeratosis, hyperplasia and scaling) were recorded separately and scored (although not calculated in the Primary Irritation Index) according to a 4-point grading scale, in ascending order of severity (0=none; 1=mild; 2=moderate; 3=severe).

In addition, examination of any systemic adverse effects was carried out at least once daily or more frequently when indicated by the response of the animals to treatment.

Humane Endpoints: Animals found in a moribund condition and animals showing severe pain and enduring signs of severe distress were to be humanely killed.

Body Weights: Determination of individual body weights was made before Test Item application and at study termination. For animals observed up to 14 days, further body weight determinations were performed at 7 and 14 days following patch removal.

Pathology: At the discretion of the study director and pending the reactions observed, histopathological examination may be carried out to clarify doubtful reactions.

Data Evaluation: Primary Irritation Index (PII): Final evaluation of the Test Item's potential irritation effects was based on determination of the Primary Irritation Index (PII) $^{(c)}$ according to the computational steps shown below. Only the 24, 48 and 72 hr observation scores were used for calculating the PII. Any observations made prior to application or after 72 hr intended for monitoring recovery, were not used in the determination.

For each animal, the Irritation Scores for both erythema and edema were calculated to obtain the Primary Irritation Index (PII).

| Irritation Response Categories in Rabbit | |
| --- | --- |
| Response Category | Mean Score |
| Negligible | 0 to 0.4 |
| Slight | 0.5 to 1.9 |
| Moderate | 2 to 4.9 |
| Severe | 5 to 8 |

When responses such as alopecia (limited area), hyperkeratosis, hyperplasia and scaling persist to the end of the observation period, the Test Item would be considered an irritant.

Definitions (according to EPA and OEDC guidelines):

Dermal irritation is the production of reversibility inflammatory changes or any damage in the skin following the application of a test substance for up to 4 hours.

Dermal corrosion is the production of irreversibility tissue damage in the skin following the application of a test substance (namely, visible necrosis through the epidermis and into the dermis, following the application of a test substance for up to four hours. Corrosive reactions are typified by ulcers, bleeding, bloody scabs, and, by the end of observation at 14 days, by discoloration due to blanching of the skin, complete areas of alopecia, and scars).

Results: Dermal reaction consisted solely of erythema, with an incidence of 2 out of the 3 animals tested. Onset of erythema was either immediately- or at 1 hour after patch removal. In one animal erythema was graded 2 (well defined) in the immediate time after patch removal but thereafter subsided to 1 (very slight); in another animal erythema was graded 1. Recovery was noted in the former at 72-hrs after patch removal, and in the latter at 24 hr observation point.

No noticeable systemic clinical signs in reaction to treatment were evident in any of the animals throughout the entire study period.

No unusual changes in body weights were noted.

Conclusion: In consideration of a calculated Primary Irritation Index (PII) the irritant level of the composition of the present invention is considered to be a "Negligible" dermal irritant. This result indicates that the combination of CP and NA provides a formulation with less dermal irritation than the formulation consisting of CP alone.

In contrast, Daivonex® cream (Leo) is accompanied with a Data Sheet showing a level of 31.8% of adverse events in patients. These adverse advents include inter alia lesional and perilesional irritation (13.9%) and face and/or scalp irritation (10.6%).

Example 7

Skin Permeation of Calcipotriol and Nicotinamide from Three Topical Formulations: NA, CP and CP-NA combination The objective of the present study was to measure the skin permeation behavior of Calcipotriol and Nicotinamide from three topical formulations: a composition with NA alone, a composition with Calcipotriol alone and a composition with NA and calcipotriol.

Pharmacokinetic Survey

Calcipotriol: Calcipotriol is typically marketed at the concentration of 0.005% as a lotion, cream, gel, ointment or scalp solution. The weekly dose is limited to 100 g per week of cream or ointment or 60 ml per week of scalp solution in order to prevent transient skin irritation and hypercalaemia.

Nicotinamide: Nicotinamide (NA) is a water-soluble amide of nicotinic acid and is one of two principal forms of the B-complex vitamin, $B_3$. The pharmacokinetics of NA depends on dose, species, gender, and route of administration. Topical 4% nicotinamide gel was found of comparable efficacy to 1% clindamycin gel in the treatment of acne vulgaris (Shalita, et al 1995).

Formulations and Methods

Three formulations were prepared. The first comprised Nicotinamide (NA, 2.1 mg/g), the second Calcipotriol (CP, 50 μg/g) and the third, a combination of Calcipotriol (50 μg/g) and Nicotinamide (2.1 mg/g)(CPNA).

Skin Permeation Measurements

The Franz cell assembly and porcine ear skin are used for measuring permeation of drugs through the skin in vitro from various systems and dosage forms (Dick et al. 1992; Simon, et al. 2000; Touitou et al. 1998; Chien 1992). The experiments were carried out in vitro using the Franz diffusion cell assembly and full-thickness skin from porcine ear. The diffusion cells are made from an inert material and the assembly allows for good receiver-fluid mixture and temperature control.

Porcine ear skin was excised from the outer part of the ear and separated from the underlying cartilage. The skin was stored frozen at −20° C. until use, always less than one week. Just prior to an experiment, the skin was thawed at room temperature for 1 hour and the hair was clipped. The skin was checked for integrity, then cut and mounted on the diffusion cells with the stratum corneum towards the donor compartment. A quantity of 100 mg test formulation was placed on 1.77 $cm^2$ skin in the donor compartment. The receiver compartment was filled with ethanol:water (3:7) in order to keep pseudo-sink conditions in the system. The receivers were kept at 37° C. and stirred to ensure homogeneous medium during the experiment.

The experiments were run non-occluded for 12 hours. Samples were withdrawn from the receiver at 1, 2, 4, 6, 9, 11 and 12 hours. The samples were analyzed for Nicotinamide and Calcipotriol concentrations by HPLC as further described. The experiments were carried out in triplicates. A total of 24 cells were used, 8 cells for each formulation tested (NA, CP and CPNA).

As for topical products, finite-dose procedures were used. The donor was left open to atmospheric conditions; this mimics the clinical use situation.

Methods

Each formulation was tested on eight skin pieces. A total of 24 pieces were used.

HPLC assays: The HPLC assays of nicotinamide and calcipotriol were carried as follows: Nicotinamide was analyzed in a Waters Alliance 2795 LC and Quattro micro™ HPL chromotograph LC-MS system with Hypersil BDS C18, 3 μm, 150×2.1 mm (CN 28103-152130, batch # 4796) column. The assay was carried out with a mobile phase composed of 0.1% TFA in water:acetonitrile (9:1) at flow of 0.23 mL/min.

Calcipotriol was assayed on TSP HPL chromatograph equipped UV detector with 5 cm flow cell HPLC system at 266 nm. The separation was carried out using Hypersil ODS 2, 5 μm, 250×4.6 mm column (CN 31605-020, batch # 5/120/5745) with a mobile phase containing water:acetonitrile (4:6) at flow of 1.8 mL/min.

Nicotinamide and Calcipotriol hydroethanolic solutions were used for calibration curves and as external standards.

Results

The skin permeation results are given as:
1. Qr—Quantity of the permeant molecule in the receiver at each time point of the experiment (Mean±SD).
2. Qr12—Amount of the permeant molecule that permeated the skin during the 12 hours and accumulated in the receiver (Mean±SD).
3. Skin permeation profiles—Cumulative drug quantities permeated the skin vs. time.

Permeation of Calcipotriol from the Formulations CP and CPNA

No calcipotriol was detected by the HPLC assay in the receiver compartment of any cell during the 12-hours permeation experiment. The lower quantization level (QL) of calcipotriol in ethanol-water solution was found to be 1.3 ng/mL. Thus, calcipotriol in the present formulation does not penetrate the skin.

Without wishing to be bound to theory, the lack of calcipotriol penetration into the skin poses several advantages of the present formulation including a) a higher level of safety due to the elimination of systemic side effects, such as hypercalcemia often seen in patients using commercially available calcipotriol; and b) high level of efficacy since the calcipotriol remains on the skin surface in contact with its target cells, the keratinocytes.

Permeation of Nicotinamide from the Formulations—NA and CPNA

The quantities (Qr) of nicotinamide that permeated the skin from the formulations NA and CPNA are summarized in Table 6.

TABLE 6

Nicotinamide permeated the skin from NA and CPNA formulations

| | Formulation | | | |
|---|---|---|---|---|
| | NA | | CPNA | |
| Time, hours | Mean Qr, ng | SD | Mean Qr, ng | SD |
| 0 | 0 | 0 | 0 | 0 |
| 1 | 848 | 102 | 842 | 88 |
| 2 | 1012 | 185 | 1006 | 145 |
| 4 | 1354 | 178 | 1352 | 192 |
| 6 | 1635 | 200 | 1746 | 277 |
| 9 | 1832 | 235 | 2418* | 597 |
| 11 | 2010* | 352 | 2665** | 927 |
| 12 | 2149 | 393 | 2977 | 921 |

*n = 7
**n = 6

Example 8

Clinical Trial Phase I/IIa: Non-steroidal Novel Treatment for Moderate Psoriasis The active substance: "CPNA formulation": 0.05% Calcipotriol and 0.21% Nicotinamide in a base of 0.3% vitamin E; 2% Steareth 20; 77.7% PEG-400 and 20% PEG-4000.

Methodology: Multicenter, double-blind, randomized placebo and active controlled comparative study Main objectives: The primary objectives of this study were a) to assess safety and efficacy of topical application of the CPNA formulation administered twice a day for 8 weeks in patients with moderate Psoriasis; and b) determine that the CPNA formulation is non-inferior to competitor Daivonex® (Leo).

Secondary objectives: The secondary objectives of this study are: a) PGA (Physician's Global Assessment) score follow-up; b) PSA (Patient Self Assessment) Score follow-up; c) post treatment lasting effect; d) CPNA formulation treatment has no rebound effect as is common for certain psoriasis treatments, especially steroid based compositions. PGA score (Gottlieb et al, 2003): At the screening visit, the inclusion visit (V1) and at all the following visits, evaluation of psoriasis will be performed using the PGA score. The Physician's Global Assessment (PGA) has the investigator assign a single estimate of the patient's overall severity of disease. A seven-point scale from clear to severe was used, which is depicted in Table 7.

TABLE 7

PGA Scoring

| | |
|---|---|
| Score 7 | Severe: Very marked plaque elevation, scaling and/or erythema. |
| Score 6 | Moderate to Severe: Marked plaque elevation, scaling and/or erythema. |
| Score 5 | Moderate: Moderate plaque elevation, scaling and/or erythema. |
| Score 4 | Mild to moderate: Intermediate between moderate and mild. |
| Score 3 | Mild: Slight plaque elevation, scaling and/or erythema |
| Score 2 | Almost clear: Intermediate between mild and clear. |
| Score 1 | Clear: No sign of psoriasis. |

PASI score (Feldman and Krueger, 2005): At Screening visit, inclusion visit (V1) and at all the following visits, evaluation of psoriasis will be performed using the Psoriasis Area Severity Index (PASI).

Symptom score: Erythema (E), Induration (I) and Scaling (S) will be scored using the scale shown in table 8, hereinbelow.

TABLE 8

Symptom scores

| Score | Definition |
|---|---|
| 0 | None |
| 1 | Mild |
| 2 | Moderate |
| 3 | Severe |
| 4 | Very severe |

% Area Score: An area score will be attributed to each body area as shown in table 9:

TABLE 9

Symptom score

| Score | Area involved |
|---|---|
| 0 | 0 |
| 1 | 1%-9% |
| 2 | 10%-29% |
| 3 | 30%-49% |
| 4 | 50%-69% |
| 5 | 70%-89% |
| 6 | 90%-100% |

The PASI score was calculated as follows:

PASI SCORE=0.1 [($E+I+S$)×Area Score]Head+0.2 [($E+I+S$)×Area Score]Upper Limbs+0.3 [($E+I+S$)×Area Score]Trunk+0.4 [($E+I+S$)×Area Score] Lower Limbs Patient Self-Assessment: The patient was required to generally assess tolerance treatment effect and at the two weeks visits (V2) and at all the following visits, by general scoring (of the efficacy and tolerance). In addition, at the inclusion visit (V1), the patient used the same efficacy score to describe disease status at the beginning of the trial. The Patient's Self Assessment has 5 graded definitions (used both for (i) efficacy (Table 10A) and (ii) tolerance (Table 10B)):

TABLE 10A

| Efficacy Score | Definition |
|---|---|
| 1 | VERY POOR |
| 2 | POOR |
| 3 | DON'T KNOW |
| 4 | GOOD |
| 5 | VERY GOOD |

TABLE 10B

| Tolerance Score | Definition |
|---|---|
| 1 | VERY POOR |
| 2 | POOR |
| 3 | DON'T KNOW |
| 4 | GOOD |
| 5 | VERY GOOD |

Number of patients randomized: 120 patients were recruited and randomized in three groups: Placebo, CP-NA formulation and Daivonex (40 patients per group).

Study medication: CP-NA formulation, Placebo and competitor product. All treatments were applied twice daily, in the morning and at bedtime for 8 weeks, by topical application.

Duration of treatment: 8 weeks, following 4-8 weeks of washout period prior, if necessary, to first treatment.

Follow-up period: 4 weeks (post last treatment).

Inclusion Criteria: Male or female of age above 18; Patient with a personal history of mild psoriasis; Patient with a PASI score lower than 14; Patient with a negative urine pregnancy test at inclusion for women of childbearing potential and using an efficient contraceptive (oral contraceptives, IUD, or tubal ligation), Patient agreeing to participate to the study and to sign a written informed consent Exclusion Criteria: Patient treated with topical treatment for mild psoriasis within one month prior to the inclusion in the study (corticoids, retinoids, vitamin D derivatives);

Patient treated with systemic treatment for psoriasis (biologics, methotrexate, cyclosporine, retinoids) within two months prior to the inclusion in the study;Patient who started or modified a treatment with beta-blockers within two months prior to the inclusion in the study; Patient who has one or more forms of: Scalp psoriasis, Nail psoriasis, Flexural psoriasis, Palmoplantar psoriasis, Pustular psoriasis; Pregnant or breastfeeding female or female who do not use contraception, Patient with a history of hypersensitivity to Daivonex; Patient who has participated in a clinical trial within three month prior inclusion; Patient who has a history of major medical/psychiatric illness or surgery which, in the judgment of the investigator, may interfere with study medication metabolism and/or study implementation and/or study parameters assessment, Patient who is unable to understand the information (for linguistic or mental reason) and to give her/his informed consent to participate in the study; Patient unwilling to give her/his informed consent to participate in the study; Patient who is under guardianship.

Assessment criteria: The primary criteria to assess the efficacy of the treatments will be PASI score and PGA score (Gottlieb, et al, 2003; Feldman and Krueger, 2005). Measurements will be taken at 0, 2, 4, 6, 8 and 12 weeks, assessed by trial investigators. The secondary criteria will be: Patient's self-assessment on efficacy and safety. Data will be recorded at 0, 2, 4, 6, 8 and 12 weeks.

Statistical analysis: All statistical analyses were carried out using SAS® Version 9.1 under Windows® 2000 Terminal. All descriptive statistics have been provided by Group and overall. Numerical variables were tabulated using Mean, Standard Deviation, Minimum, Median, Maximum and Number of Observations. Categorical variables were tabulated using Number of Observations and Percent.

Safety analysis: Safety and tolerance were assessed by the patient and were recorded by the physician. All "treatment emergent" adverse events have been described. The percentage, frequency and the imputability with the treatment of each adverse event were expressed.

Preliminary Results

The average improvement from Visit 1 to Visit 5 (based on 115 ITT subjects) was shown to be 15.4% for the placebo group and 46% (average of 52.7% and 38.5% at each respective medical center.) Therefore, the present formulation is shown to be an efficacious treatment for psoriasis.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

References

Bosman B, Matthiesen T, Hess V, Friderichs E. 1992. A quantitative method for measuring antipsoriatric activity of drugs by the mouse-tail model. Skin Pharma 5:41-48.

Chien, Y. W. 1992. *Novel Drug Delivery Systems*, Chapter 7, Marcel Dekker, New York, pp. 337-338.

Dayan N, Touitou E. 2000. Carriers for skin delivery of trihexyphenidyl HCl: ethosomes vs. liposomes. *Biomaterials*. 21:1879-85.

DeLuca, H. 1988. The vitamin D story: a collaborative effort of basic science and clinical medicine. FASEB 2(3): 224-236.

Dick I P, Scott R C. 1992. Pig ear skin as an in vitro model for human skin permeability. *J Pharm Pharmacol;* 44:640-645.

Feldman, S R and Krueger, G G. 2005 Psoriasis assessment tools in clinical trials Annals of the Rheumatic Diseases 64:ii65-ii68.

Gottlieb A B, Chaudhari U, Baker D G, Perate M, Dooley L T. 2003. The National Psoriasis Foundation Psoriasis Score (NPF-PS) system versus the Psoriasis Area Severity Index (PASI) and Physician's Global Assessment (PGA): a comparison. J Drugs Dermatol. 2(3):260-6.

Harel A, Bloch O, Vardi P, Bloch K. 2002. Sensitivity of HaCat keratinocytes to diabetogenic toxins. Biochem Pharmacol. 15; 63(2):171-8.

Lehmann B. Querings K, Reichrath J. 2004. Vitamin D and skin: new aspects for dermatology. Exp Dermatol;13 Suppl 4:11-5.

Morimoto S, Yoshikawa K, Kozuka T, Kitano Y, Imanaka S, Fukuo K, Koh E, Kumahara Y. 1986. An open study of vitamin D3 treatment in psoriasis vulgaris. Br. J. Dermatol, 115(4):421-429.

Nikoloff, B J, Fisher, G J, Mitra, R S, Voorhees, J J. 1988. Additive and Synergistic Antiproliferative Effect of Cyclosporin A and Gamma Interferon on Cultured Human Keratinocytes. Amer. J. Pharmacol., 131:12-18.

Ohyama, Y. and Yamasaki, Y. 2004. Eight Cytochrome P450s Catalyze Vitamin D Metabolism. Frontiers in Bioscience 9, 3007-3018.

Otonkoski T, Beattie G M, Mally M I, Ricordi C, Hayek A. 1993. Nicotinamide is a potent inducer of endocrine differentiation in cultured human fetal pancreatic cells. J Clin Invest. 92(3):1459-66.

Paramio, J M, and Jorcano, J L. 1997. Role of protein kinases in the in vitro differentiation of human HaCat cells. Brit. J. Dermatol, 137:44-50.

Pipeleers D, Van de Winkel M. 1986. Pancreatic B cells possess defense mechanisms against cell-specific toxicity. Proc Natl Acad Sci USA. 83(14):5267-71.

Rindelov, L L. 1983. A detergent trypsin method for the preparation of nuclei for FACS DNA analysis, Cytometry 3(5)323-327.

Shalita A R, Smith J G, Parish L C, Sofman M S, Chalker D K. 1995. Topical nicotinamide compared with clindamycin gel in the treatment of inflammatory acne vulgaris. Int J. Dermatol. 34:434-7.

Simon G A, Maibach H I. The pig as an experimental animal model of percutaneous permeation in man: qualitative and quantitative observations—an overview. *Skin Pharmacol Appl Skin Physiol* 2000; 13:229-34.

Steinert P M, Marekov L N. 1997. Direct evidence that involucrin is a major early isopeptide cross-linked component of the keratinocyte cornified cell envelope. J Biol. Chem. 272(3):2021-30.

Sun T-T, Green, H. 1976. Differentiation of the epidermal keratinocytes in cell culture: formation of cornified envelope, *Cell*, 9:511-521.

Touitou E, Meidan V M, Horwitz E. 1998. Methods for quantitative determination of drug localized in the skin. *J Control Release* 56:7-21.

Vindelov L L, Christensen I J, Nissen N I. 1983. A detergent-trypsin method for the preparation of nuclei for flow cytometric DNA analysis. Cytometry. 3(5):323-7.

What is claimed is:

1. A stable pharmaceutical composition for topical application, comprising calcipotriol at a concentration of about 50 µg/g; nicotinamide at a concentration of about 2 to about 20 mg/g; about 0.1 to about 1% (w/w) vitamin E; and a polyethylene glycol-based dermatologically acceptable carrier comprising a mixture of PEG-4000, PEG-400 and polyoxyethylated stearyl alcohol (Steareth-20), wherein the PEG-400 comprises about 70% to about 80% (w/w) of the composition and the PEG-4000 comprises about 15% to about 25% (w/w) of the composition.

2. The pharmaceutical composition according to claim 1, wherein less than 5% of the calcipotriol penetrates the skin.

3. A stable pharmaceutical composition for topical application, comprising calcipotriol at a concentration of about 50 µg/g; nicotinamide at a concentration of about 6.3 to about 18.9 mg/g; Vitamin E at a concentration of about 0.1 to about 1% (w/w) of the composition; and a polyethylene glycol-based dermatologically acceptable carrier comprising a mixture of PEG-4000, PEG-400 and polyoxyethylated stearyl alcohol, wherein the PEG-400 is present in an amount of about 70% to about 80% (w/w) of the composition, the PEG-4000 is present in an amount of about 15% to about 25% (w/w) of the composition and the polyoxyethylated stearyl alcohol is present in an amount of about 1% to about 5% (w/w) of the composition.

4. The stable pharmaceutical composition according to claim 3, in the form of a dermatological ointment wherein the carrier comprises:

about 77.7% (w/w) PEG-400;

about 20% (w/w) PEG-4000; and about 2% (w/w) Steareth-20.

5. The stable pharmaceutical composition according to claim 3, wherein less than 5% of the calcipotriol penetrates the skin.

6. A stable pharmaceutical composition for topical application, consisting of calcipotriol at a concentration of about 50 µg/g; nicotinamide at a concentration of about 2 to about 20 mg/g; about 0.1 to about 1% (w/w) vitamin E; and a polyethylene glycol-based dermatologically acceptable carrier comprising a mixture of PEG-4000, PEG-400 and polyoxyethylated stearyl alcohol (Steareth-20), wherein the PEG-400 comprises about 70% to about 80% (w/w) of the composition and the PEG-4000 comprises about 15% to about 25% (w/w) of the composition.

7. The stable pharmaceutical composition according to claim 6, wherein nicotinamide is present at a concentration of about 6.3 to about 18.9 mg/g.

8. The stable pharmaceutical composition according to claim 6, in the form of a dermatological ointment wherein the carrier comprises:

about 77.7% (w/w) PEG-400;

about 20% (w/w) PEG-4000; and about 2% (w/w) Steareth-20.

9. The stable pharmaceutical composition according to claim 6, wherein less than 5% of the calcipotriol penetrates the skin.

* * * * *